US012106217B2

(12) United States Patent
Creed et al.

(10) Patent No.: US 12,106,217 B2
(45) Date of Patent: Oct. 1, 2024

(54) GRAPH NEUTRAL NETWORKS WITH ATTENTION

(71) Applicant: BENEVOLENTAI TECHNOLOGY LIMITED, London (GB)

(72) Inventors: Paidi Creed, London (GB); Aaron Sim, London (GB); Amir Alamdari, London (GB); Joss Briody, London (GB); Daniel Neil, Williamsburg, VA (US); Alix Lacoste, Brooklyn, NY (US)

(73) Assignee: BenevolentAI Technology Limited, London (GB)

( * ) Notice: Subject to any disclaimer, the term of this patent is extended or adjusted under 35 U.S.C. 154(b) by 838 days.

(21) Appl. No.: 17/041,625

(22) PCT Filed: May 16, 2019

(86) PCT No.: PCT/GB2019/051352
§ 371 (c)(1),
(2) Date: Sep. 25, 2020

(87) PCT Pub. No.: WO2019/220128
PCT Pub. Date: Sep. 21, 2019

(65) Prior Publication Data
US 2021/0081717 A1 Mar. 18, 2021

Related U.S. Application Data

(60) Provisional application No. 62/673,554, filed on May 18, 2018.

(51) Int. Cl.
*G06K 9/00* (2022.01)
*G06F 17/16* (2006.01)
(Continued)

(52) U.S. Cl.
CPC .............. *G06N 3/082* (2013.01); *G06F 17/16* (2013.01); *G06F 18/2148* (2023.01);
(Continued)

(58) Field of Classification Search
CPC .......... G06N 3/045; G06N 3/08; G06N 3/044; G06N 5/022; G06N 3/084; G06N 3/047;
(Continued)

(56) References Cited

U.S. PATENT DOCUMENTS 9,965,705 B2    5/2018  Chen et al.

OTHER PUBLICATIONS

Veličković, Graph Attention Networks, arXiv, Feb. 2018 (Year: 2018).*

(Continued)

*Primary Examiner* — Alex Kok S Liew
(74) *Attorney, Agent, or Firm* — Smith Baluch LLP

(57) ABSTRACT

Methods and apparatus are provided for generating a graph neural network (GNN) model based on an entity-entity graph. The entity-entity graph comprising a plurality of entity nodes in which each entity node is connected to one or more entity nodes of the plurality of entity nodes by one or more corresponding relationship edges. The method comprising: generating an embedding based on data representative of the entity-entity graph for the GNN model, wherein the embedding comprises an attention weight assigned to each relationship edge of the entity-entity graph; and updating weights of the GNN model including the attention weights by minimising a loss function associated with at least the embedding; wherein the attention weights indicate the relevancy of each relationship edge between entity nodes of the entity-entity graph. The entity-entity graph may be filtered based on the attention weights of a trained GNN model. The filtered entity-entity graph may be used to update the GNN model or train another GNN model. The (Continued)

trained GNN model may be used to predict link relationship between a first entity and a second entity associated with the entity-entity graph.

18 Claims, 16 Drawing Sheets

(51) Int. Cl.
- *G06F 18/214* (2023.01)
- *G06N 3/047* (2023.01)
- *G06N 3/08* (2023.01)
- *G06N 3/082* (2023.01)
- *G06N 5/02* (2023.01)

(52) U.S. Cl.
CPC ............... *G06N 3/047* (2023.01); *G06N 3/08* (2013.01); *G06N 5/02* (2013.01)

(58) Field of Classification Search
CPC ........ G06N 3/04; G06N 3/048; G06N 3/0464; G06N 3/088; G06N 20/00; G06N 5/02; G06N 3/042; G06N 3/0455; G06N 3/09; G06N 7/01; G06N 3/0442; G06N 5/01; G06N 3/006; G06N 3/082; G06N 20/10; G06N 3/063; G06N 3/02; G06N 3/092; G06N 3/0475; G06N 3/096; G06N 20/20; G06N 5/04; G06N 3/049; G06N 3/0895; G06V 10/82; G06V 10/751; G06V 10/764; G06V 30/10; G06V 10/426; G06V 10/761; G06V 20/41; G06V 20/69
See application file for complete search history.

(56) References Cited

OTHER PUBLICATIONS

Thekumparampil, Attention-based Graph Neural Network for Semi-supervised Learning, arXiv, Mar. 2018 (Year: 2018).*
PCT Written Opinion and Search Report issued in related PCT Patent Application No. PCT/GB2019/051352 mailed Jul. 29, 2019.
Chao, Shang, et al., "Edge Attention-based Multi-Relational Graph Convolutional Networks", arxiv>org, Cornell University Library, 201 Olin Library Cornell University, dated Feb. 14, 2018, 10 pgs.
Teney, Damien, et al., "Graph-Structured Representations for Visual Question Answering", IEEE Computer Society Conference on Computer Vision and Pattern Recognition Proceedings, IEEE Computer Society, Jul. 21, 2017, 9 pgs.

* cited by examiner

GRAPH NEUTRAL NETWORKS WITH ATTENTION

CROSS-REFERENCE TO RELATED PATENT APPLICATIONS

This patent application is the 35 U.S.C. 371 national stage of International Patent Application PCT/GB2019/051352 filed 16 May 2019; which claims the benefit of priority to U.S. Provisional Application 62/673,554 filed 18 May 2018, which is incorporated by reference herein for all purposes.

The present application relates to apparatus, system(s) and method(s) for graph neural networks (GNN) and GNN models with attention.

BACKGROUND

Many relevant inference problems that have immediate practical applications can be formulated as a link prediction task leveraging prior graph-structured information. For example, predicting winners in football, possible therapeutic targets for diseases, or inferences on entities on Wikipedia can all be cast as link prediction tasks that make use of graph-structured data to inform the prediction. Large-scale databases of facts can be represented as a entity-entity knowledge graph, which is a graph structure describing relationships between entity nodes, that is used to form the basis of a prediction or increase prediction quality, and offer facts in the universal form of the graph triple e=(s,r,o) that relates a subject entity node s through a relation edge r to an object entity node o of the knowledge graph. The study of the proper way to predict novel links (a.k.a. connections)—the link prediction task—on this implied graph structure is a major area of study in statistical relational learning.

Despite the fact that link prediction is an inherently graph-formulated task, algorithms that are able to efficiently ingest a graph structure to perform prediction have arrived relatively recently. Interest in making predictions on graph-ingested data has increased after the initial success of deep neural networks such as, by way of example only but is not limited to, deep convolutional neural networks (CNN). The efforts to extend those extremely successful models to support graph data while still offering efficient transforms on neighbourhoods around nodes are typically divided into two classes of approaches. The first set of methods, referred to as spectral approaches, bootstraps the insight that a convolution can be defined in the Fourier domain by computing operations on the Laplacian eigenbasis, and now provide methods for learning spatially-localized filters dependent on the graph structure. The second class of methods, non-spectral, define convolutions directly on the graph, but the challenge remains of offering an operation that is invariant to edge order and node degree. Approaches such as separating learned weights by node degree, extracting and normalising a fixed number of nodes, or sampling through a recurrent architecture have found successful applications recently. However, in nearly all of these approaches, the weights of the model transform the features on the nodes, while a link weight is usually a function of the connectivity of that node.

Graph neural network (GNN) models based on, by way of example only but are not limited to, graph convolutional neural networks (GCNNs) have recently been used to model link prediction and/or classification problems based on multimodal entity-entity knowledge graph structures and the like. Although some researchers have reported significant gains in modelling particular problems, most of these have relied upon carefully vetted graph-based training datasets. However, conventional GCNN models are unable to ignore or remove noise from less useful relationship edges or entity nodes present in the initial entity-entity knowledge graph. This has a significant negative impact on the performance of the resulting graph model (e.g. link prediction graph model) that is generated by the GCNN based on the graph-based training dataset.

Although GCNNs are more efficient than traditional approaches, most conventional GCNNs are typically susceptible to noisy or incorrect graph-based datasets that lead to worsening performance compared with traditional neural network approaches. This problem is exacerbated for deep learning that requires extremely large-scale datasets that are difficult or too costly to verify due to the sheer size of the datasets derived from large-scale databases of facts. Although traditional approaches can ingest large-scale databases of facts in a non-graph structured manner, they are costly in terms of computational complexity. There is a desire to overcome the shortcomings of GCNNs, or for that matter most GNNs, and modify such techniques to handle or even identify and explicitly or implicitly filter out noisy or incorrect data within an entity-entity knowledge graph structured dataset of a database of facts and hence efficiently generate a robust GNN model (e.g. a link-prediction GNN model).

The embodiments described below are not limited to implementations which solve any or all of the disadvantages of the known approaches described above.

SUMMARY

This Summary is provided to introduce a selection of concepts in a simplified form that are further described below in the Detailed Description. This Summary is not intended to identify key features or essential features of the claimed subject matter, nor is it intended to be used to determine the scope of the claimed subject matter; variants and alternative features which facilitate the working of the invention and/or serve to achieve a substantially similar technical effect should be considered as falling into the scope of the invention disclosed herein.

Methods and apparatus are provided for generating a graph neural network (GNN) model based on an entity-entity graph. The entity-entity graph comprising a plurality of entity nodes in which each entity node is connected to one or more entity nodes of the plurality of entity nodes by one or more corresponding relationship edges. The method comprising: generating an embedding based on data representative of the entity-entity graph for the GNN model, wherein the embedding comprises an attention weight assigned to each relationship edge of the entity-entity graph; and updating weights of the GNN model including the attention weights by minimising a loss function associated with at least the embedding; wherein the attention weights indicate the relevancy of each relationship edge between entity nodes of the entity-entity graph. The entity-entity graph may be filtered based on the attention weights of a trained GNN model. The filtered entity-entity graph may be used to update the GNN model or train another GNN model. The trained GNN model may be used to predict link relationship between a first entity and a second entity associated with the entity-entity graph.

In a first aspect, the present disclosure provides a computer-implemented method for training a graph neural network (GNN) model based on an entity-entity graph for relationship prediction, the entity-entity graph comprising a plurality of entity nodes in which each entity node is connected to one or more entity nodes of the plurality of entity nodes by one or more corresponding relationship edges, the method comprising: generating an embedding based on data representative of at least a portion of the entity-entity graph for the GNN model, wherein the embedding comprises an attention weight assigned to each relationship edge of at least the portion of the entity-entity graph; and updating the GNN model including the attention weights by minimising a loss function associated with at least the embedding; where the attention weights indicate the relevancy of each corresponding relationship edge between entity nodes of the entity-entity graph and assist the GNN model in relationship prediction.

Preferably, the computer-implemented method further comprising: generating one or more relationship scores based on data representative of one or more embedding(s) associated with the portion of entity-entity graph; where updating the GNN model further includes updating the GNN model including the attention weights by minimising the loss function based on at least the embedding and the relationship scores.

Preferably, the computer-implemented method further comprising repeating the steps of generating the embedding and/or scoring, and updating the weights until the GNN model is determined to be trained.

Preferably, the embedding is based on data representative of one or more from the group of: at least a portion of the entity-entity graph for the GNN model; the entity-entity graph for the GNN model; one or more rules defining actions in relation to relationship edges; one or more rules defining actions in relation to entity nodes; and one or more rules for including or excluding certain relationship edges or entity nodes.

Preferably, the GNN model is based on one or more neural networks from the group of: one or more artificial NNs; one or more feedforward NNs; one or more recursive NNs; Convolutional NNs; graph NNs; graph CNNs; autoencoder NNs; one or more neural networks capable of being trained based on data representative of the entity-entity graph.

Preferably, an entity node in the entity-entity graph represents any entity from the group of: disease; compound/drug; protein; biological entity; pathway; biological process; cell-line; cell-type; symptom; clinical trials; any other biomedical concept; or any other entity with at least an entity-entity relationship to another entity in the entity-entity graph.

Preferably, the computer-implemented method further comprising outputting the trained attention weights from the GNN model.

Preferably, the computer-implemented method further comprising generating a filtered entity-entity graph by weighting each edge with a corresponding trained attention weight.

Preferably, the computer-implemented method further comprising: updating the GNN model based on the filtered entity-entity graph.

Preferably, the computer-implemented method further comprising: predicting link relationships between entities in the filtered entity-entity relationship graph by inputting to the updated graph model representations of two or more entities; and receiving an indication of the likelihood of a link relationship existing between the two or more entities.

Preferably, the computer-implemented method further comprising: predicting link relationships between entities by inputting to the GNN model representations of two or more entities; and receiving an indication of the likelihood of a link relationship existing between the two or more entities.

Preferably, the computer-implemented method as claimed in any preceding claim, where minimising the loss function, $\mathcal{L}(\bullet)$, further comprising: assigning an attention weight, $\alpha_{r,i,j}$, to each relationship edge of the entity-entity graph, wherein $\alpha_{r,i,j}$ is the attention weight associated with the connection between entity node i and entity node j with relation index r of the plurality of relationships associated with the entity-entity graph; modifying the loss function by adding an attention loss function, $\mathcal{L}_{att}(\hat{\Lambda})$, associated with the set of attention weights $\hat{\Lambda}=\{\alpha_{r,i,j}\}$ to the loss function; and minimising the modified loss function, $\mathcal{L}_{mod}$, with respect to the weights of the GNN model including the attention weights; where the modified loss function is $\mathcal{L}_{mod}(\bullet)=\mathcal{L}(\bullet)+\mathcal{L}_{att}(\hat{\Lambda})$.

Preferably, the computer-implemented method further comprising regularising each of the updated attention weights $\alpha_{r,i,j}$, to a normalised attention weight $\alpha'_{r,i,j}$ based on:

$$\alpha'_{r,i,j} = \frac{1}{\Sigma_r \Sigma_j |\alpha_{r,i,j}|} |\alpha_{r,i,j}|$$

where the attention weight $\alpha_{r,i,j}$ is initially set to 1 and $\alpha'_{r,i,j}=1/\mathcal{N}_i$ for all j prior to training the GNN model.

Preferably, the embedding $h_i^{(l+1)}$ for entity node i and layer l+1, for $0 \le l$ is an N-dimensional vector $h_i^{(l+1)}$ defined by:

$$h_i^{(l+1)} = \sigma\left(\sum_{r \in \mathcal{R}} \sum_{j \in \mathcal{N}_i^r} \alpha_{r,i,j} W_{j,r}^{(l)} h_j^{(l)} + b_i^{(l)}\right)$$

where r is a relation index of a relationship from the set of all relationships $\mathcal{R}$ associated with the relationship edges of the entity-entity graph, and j is the index of an entity node connecting to entity node i within $\mathcal{N}_i^r$, $\mathcal{N}_i^r$ the set of all nodes that connect to entity node i for relation index r, $\alpha_{r,i,j}$ is the attention weight associated with the connection between entity node i and entity node j for relation index r, $b_i^{(l)}$ is a node-specific layer-wise bias vector applied to the embedding $h_i^{(l+1)}$, $W_{j,r}^{(l)}$ is the associated relationship adjacency matrix for the 1-th layer associated with entity node i, and $\sigma(\bullet)$ is an activation function.

Preferably, the entity-entity graph is generated from a dataset of facts in which each fact is represented by an entity connecting to another entity through a relationship.

In a second aspect, the present disclosure provides a computer-implemented method for filtering an entity-entity graph, the entity-relationship graph comprising a plurality of entity nodes in which each entity node is connected to one or more entity nodes of the plurality of entity nodes by a corresponding relationship edge, the method comprising: receiving a set of attention weights from a graph neural network, GNN, model, wherein the GNN model has been trained based on data representative of at least a portion of the entity-entity graph with an attention weight assigned to each relationship edge of the portion of entity-entity graph in which the attention weights are updated during training and are indicative of the relevancy of each corresponding relationship edge between entity nodes of the entity-entity graph; and generating a filtered entity-entity relationship graph based on weighting each relationship edge of at least the portion of entity-entity graph with the corresponding trained attention weight.

Preferably, generating the filtered entity-entity graph based on the trained attention weights further comprises removing any relationship edges from the entity-entity graph having a corresponding trained attention weight that is below or equal to an attention relevancy threshold.

Preferably, the computer-implemented method of the second aspect, further comprising: updating the GNN model based on the filtered entity-entity graph; or training another GNN model based on data representative of at least a portion of the filtered entity-entity graph.

Preferably, the computer-implemented method of the second aspect further comprising identifying uncertain relationship edges in the entity-entity graph based on a set of attention weights retrieved from a trained GNN model associated with the entity-entity graph and an attention relevancy threshold.

In a third aspect, the present disclosure provides a computer-implemented method for operating a graph neural network, GNN, model, the GNN model for predicting relationships between entities in an entity-entity graph, wherein the GNN model has been trained based on data representative of at least a portion of the entity-entity graph with an attention weight assigned to each relationship edge of at least the portion of entity-entity graph in which the attention weights are updated during training and are indicative of the relevancy of each corresponding relationship edge between entity nodes of the entity-entity graph an assist the GNN model in prediction, the method comprising: inputting to the GNN model data representative of a first entity, a second entity and a relationship; and receiving a score from the GNN model indicating the likelihood of the first and the second entity having the relationship.

Preferably, the computer-implemented method the third aspect further comprising training or updating the GNN model by: generating an embedding based on data representative of the entity-entity graph for the GNN model, wherein the embedding comprises an attention weight assigned to each relationship edge of the entity-entity graph; and updating the GNN model including the attention weights by minimising a loss function associated with at least the embedding.

Preferably, the computer-implemented method of the third aspect, further comprising: generating one or more relationship scores based on data representative of one or more embedding(s) associated with the entity-entity graph; where updating the GNN model further includes updating the GNN model including the attention weights by minimising the loss function based on at least the embedding and the relationship scores.

Preferably, the computer-implemented method of the third aspect further comprising repeating the steps of generating the embedding and/or scoring, and updating the weights until the GNN model is determined to be trained or updated.

Preferably, the computer-implemented method of the third aspect further comprising outputting the trained attention weights from the GNN model for downstream use.

Preferably, the computer-implemented method of the third aspect further comprising generating a filtered entity-entity graph by weighting edges of the entity-entity graph with a corresponding trained attention weight.

Preferably, the computer-implemented method of the third aspect further comprising: updating the GNN model based on the filtered entity-entity graph.

Preferably, the computer-implemented method of the third aspect further comprising: predicting link relationships between entities in the filtered entity-entity relationship graph by inputting to the graph model representations of two or more entities; and receiving an indication of the likelihood of a link relationship existing between the two or more entities.

In a fourth aspect, the present disclosure provides a graph neural network (GNN) based on an entity-entity graph for relationship prediction, the entity-entity graph comprising a plurality of entity nodes in which each entity node is connected to one or more entity nodes of the plurality of entity nodes by a relationship edge and the GNN comprising an encoder network and an updating module, the encoder network coupled to the updating module, wherein: the encoder network is configured to generate an embedding based on data representative of at least a portion of the entity-entity graph, wherein the embedding comprises an attention weight assigned to each relationship edge of at least the portion of the entity-entity graph; and the updating module is configured to update the encoder network including the attention weights by minimising a loss function associated with at least the embedding; where the attention weights indicate the relevancy of each relationship edge between entity nodes of the entity-entity graph and assist the GNN in relationship prediction.

Preferably, the GNN further comprising a scoring network coupled to the encoder network and the update module, wherein the scoring network is configured to generate a scoring based on data representative of the embedding associated with the entity-entity graph and the update module is further configured to update the weights of the GNN including the attention weights by minimising a loss function associated with the embedding and the scoring.

In a fifth aspect, the present disclosure provides an apparatus for filtering an entity-entity graph, the entity-entity graph comprising a plurality of entity nodes in which each entity node is connected to one or more entity nodes of the plurality of entity nodes by one or more corresponding relationship edges, the apparatus comprising a processor coupled to a communication interface, wherein: the communication interface is configured to receive a set of attention weights from a graph neural network, GNN, model, wherein the GNN model has been trained based on data representative of at least a portion of the entity-entity graph with an attention weight assigned to each relationship edge of at least the portion of the entity-entity graph in which the attention weights are updated during training and are indicative of the relevancy of each corresponding relationship edge between entity nodes of the entity-entity graph; the processor is configured to generate a filtered entity-entity graph by weighting each relationship edge of at least the portion of the entity-entity graph with the corresponding trained attention weight; and the communication interface is configured to output the filtered entity-entity graph.

In a sixth aspect, the present disclosure provides a GNN apparatus comprising a neural network for predicting relationships between entities in an entity-entity relationship graph, wherein the neural network has been trained based on data representative of at least a portion of the entity-entity graph with an attention weight assigned to each relationship edge of at least the portion of the entity-entity graph in which the attention weights are updated during training and are indicative of the relevancy of each corresponding relationship edge between entity nodes of the portion of entity-entity graph, wherein the GNN apparatus is configured to receive data representative of a first entity, a second entity and a relationship, and output a prediction score indicating the likelihood of the first and the second entity having the relationship.

Preferably, the neural network further comprising: an encoding network configured to generate an embedding based on data representative of the entity-entity graph for the GNN model, wherein the embedding comprises an attention weight assigned to each relationship edge of the entity-entity graph; and an update module configured to update the GNN model including the attention weights by minimising a loss function associated with at least the embedding.

Preferably, the neural network further comprising: an scoring network configured to generate one or more prediction or relationship scores based on data representative of one or more embedding(s) associated with the entity-entity graph; where the update module is further configured to update the GNN model including the attention weights by minimising the loss function based on at least the embedding and the relationship scores.

Preferably, the neural network is further configured to output the trained attention weights from the GNN model for downstream use.

In a seventh aspect, the present disclosure provides an apparatus comprising a processor, memory and communication interface, the processor connected to the memory and communication interface, wherein the apparatus is configured to implement one or more of the computer-implemented method(s) according to any of the first, second and/or third aspects, modifications thereof, and/or as herein described and the like.

In a eighth aspect, the present disclosure provides a graph neural network model obtained from a computer-implemented method according to any of the first, second and/or third aspects, modifications thereof, and/or as herein described and the like.

In a ninth aspect, the present disclosure provides a tangible (or non-transitory) computer-readable medium comprising data or instruction code for training a graph neural network (GNN) model based on an entity-entity graph for predicting relationships, the entity-entity graph comprising a plurality of entity nodes in which each entity node is connected to one or more entity nodes of the plurality of entity nodes by one or more corresponding relationship edges, which, when executed on one or more processor(s), causes at least one of the one or more processor(s) to perform at least one of the steps of: generating an embedding based on data representative of at least a portion of the entity-entity graph, wherein the embedding comprises an attention weight assigned to each relationship edge of at least the portion of entity-entity graph; and updating weights of the GNN model including the attention weights by minimising a loss function associated with at least the embedding; wherein the attention weights indicate the relevancy of each relationship edge between entity nodes of at least the portion of entity-entity graph.

In a tenth aspect, the present disclosure provides a tangible (or non-transitory) computer-readable medium comprising data or instruction code for filtering an entity-entity graph, the entity-entity graph comprising a plurality of entity nodes in which each entity node is connected to one or more entity nodes of the plurality of entity nodes by one or more corresponding relationship edges, which, when executed on one or more processor(s), causes at least one of the one or more processor(s) to perform at least one of the steps of: receiving, from a graph model generated according to any of the first, second and/or third aspects, modifications thereof, and/or as herein described and the like based on the entity-entity relationship graph, a set of trained attention weights; and filtering the entity-entity relationship graph by weighting each edge with the corresponding trained attention weight.

In an eleventh aspect, the present disclosure provides a computer-readable medium comprising program data or instruction code which, when executed on a processor, causes the processor to perform one or more steps of the computer-implemented method according to the first aspect, modifications thereof, and/or as herein described and the like.

In a twelfth aspect, the present disclosure provides a computer-readable medium comprising program data or instruction code which, when executed on a processor, causes the processor to perform one or more steps of the computer-implemented method according to the second aspect, modifications thereof, and/or as herein described and the like.

In a thirteenth aspect, the present disclosure provides a computer-readable medium comprising program data or instruction code which, when executed on a processor, causes the processor to perform one or more steps of the computer-implemented method according to the third aspect, modifications thereof, and/or as herein described and the like.

In a fourteenth aspect, the present disclosure provides a system comprising: a training module configured to train a GNN model based on data representative of at least a portion of an entity-entity graph, the entity-entity graph comprising a plurality of entity nodes in which each entity node is connected to one or more entity nodes of the plurality of entity nodes by one or more corresponding relationship edges, wherein the weights of the GNN model comprises an attention weight assigned to each relationship edge of at least the portion of the entity-entity graph, wherein the attention weights indicate the relevancy of each relationship edge between entity nodes of at least the portion of entity-entity graph; an entity-entity graph filtering module configured to receive, from a trained GNN model trained by the training module, a set of trained attention weights and generate a filtered entity-entity graph by weighting each edge of at least a portion of the entity-entity graph with the corresponding trained attention weight; and a prediction module configured to: retrieve a trained GNN model; input to the trained GNN model data representative of a first entity, a second entity and a relationship associated with an entity-entity graph; and receive a prediction score from the trained GNN model indicating the likelihood of the first and the second entity having the relationship.

Preferably, the training module further comprising: an embedding module configured to generate an embedding based on data representative of at least a portion of an entity-entity graph for a GNN model, wherein the embedding comprises an attention weight assigned to each relationship edge of at least the portion of the entity-entity graph; and an update module configured to update weights of the GNN model including the attention weights by minimising a loss function associated with at least the embedding; where the training module is further configured to train another GNN model or update a trained GNN model based on an associated filtered entity-entity graph.

The methods described herein may be performed by software in machine readable form on a tangible storage medium e.g. in the form of a computer program comprising computer program code means adapted to perform all the steps of any of the methods described herein when the program is run on a computer and where the computer program may be embodied on a computer readable medium. Examples of tangible (or non-transitory) storage media include disks, thumb drives, memory cards etc. and do not include propagated signals. The software can be suitable for execution on a parallel processor or a serial processor such that the method steps may be carried out in any suitable order, or simultaneously.

This application acknowledges that firmware and software can be valuable, separately tradable commodities. It is intended to encompass software, which runs on or controls "dumb" or standard hardware, to carry out the desired functions. It is also intended to encompass software which "describes" or defines the configuration of hardware, such as HDL (hardware description language) software, as is used for designing silicon chips, or for configuring universal programmable chips, to carry out desired functions.

The preferred features may be combined as appropriate, as would be apparent to a skilled person, and may be combined with any of the aspects of the invention.

BRIEF DESCRIPTION OF THE DRAWINGS

Embodiments of the invention will be described, by way of example, with reference to the following drawings, in which.

Figure 1A:
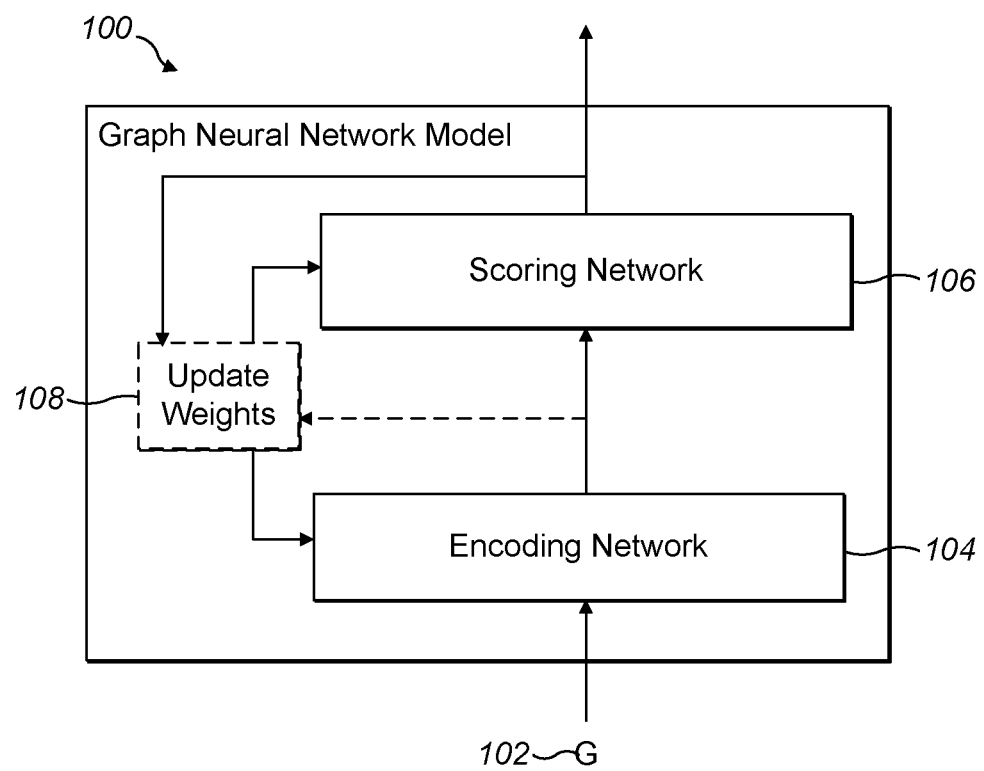
FIG. 1a is a schematic diagram illustrating an example graph neural network (GNN) model according to the invention.

Common reference numerals are used throughout the figures to indicate similar features.

DETAILED DESCRIPTION

Embodiments of the present invention are described below by way of example only. These examples represent the best mode of putting the invention into practice that are currently known to the Applicant although they are not the only ways in which this could be achieved. The description sets forth the functions of the example and the sequence of steps for constructing and operating the example. However, the same or equivalent functions and sequences may be accomplished by different examples.

The invention relates to a system, apparatus and method(s) for efficiently generating and training a robust graph neural network (GNN) model using attention weights and based on data representative of at least a portion of an entity-entity graph dataset generated from, by way of example only but not limited to, a dataset of facts and/or entity relations/relationships and the like; the GNN model may be used for prediction tasks such as, by way of example only but not limited to, link prediction or relationship inference based on the trained GNN model when trained on or extracted from noisy graph datasets; the attention weights of the trained GNN model according to the invention may be used to filter the entity-entity graph, in which the filtered entity-entity graph may be used to update the trained GNN model and/or train another GNN model for prediction tasks and the like.

An entity-entity graph comprises or represents a graph structure including a plurality of entity nodes in which each entity node is connected to one or more entity nodes of the plurality of entity nodes by one or more corresponding relationship edges, in which each relationship edge represents a relationship between a pair of entities. The term entity-entity graph, entity-entity knowledge graph, graph, or graph dataset may be used interchangeably throughout this disclosure.

An entity may comprise or represent any portion of information or a fact that has a relationship with another portion of information or another fact. For example, in the biological, chem(o)informatics or bioinformatics space(s) an entity may comprise or represent a biological entity such as, by way of example only but is not limited to, a disease, gene, protein, compound, chemical, drug, biological pathway, biological process, anatomical region or entity, tissue, cell-line, or cell type, or any other biological or biomedical entity and the like. In another example, entities may comprise a set of patents, literature, citations or a set of clinical trials that are related to a disease or a class of diseases. In another example, in the data informatics fields and the like, an entity may comprise or represent an entity associated with, by way of example but not limited to, news, entertainment, sports, games, family members, social networks and/or groups, emails, transport networks, the Internet, Wikipedia pages, documents in a library, published patents, databases of facts and/or information, and/or any other information or portions of information or facts that may be related to other information or portions of information or facts and the like. Entities and relationships may be extracted from a corpus of information such as, by way of example but is not limited to, a corpus of text, literature, documents, web-pages; distributed sources such as the Internet; a database of facts and/or relationships; and/or expert knowledge base systems and the like; or any other system storing or capable of retrieving portions of information or facts (e.g. entities) that may be related to (e.g. relationships) other information or portions of information or facts (e.g. other entities) and the like.

For example, in the biological, chem(o)informatics or bioinformatics space(s), an entity-entity graph may be formed from a plurality of entities in which each entity may represent a biological entity from the group of: from the disease, gene, protein, compound, chemical, drug, biological pathway, biological process, anatomical region or entity, tissue, cell-line, or cell type, clinical trials, any other biological or biomedical entity and the like. Each of the plurality of entities may have a relationship with another one or more entities of the plurality of entities. Thus, an entity-entity graph may be formed with entity nodes including data representative of the entities and relationship edges connecting entities including data representative of the relations/relationships between the entities. The entity-entity graph may include a mixture of different entities with relationships therebetween, and/or may include a homogenous set of entities with relationships therebetween.

Although details of the present disclosure may be described, by way of example only but is not limited to, with respect to biological, chem(o)informatics or bioinformatics entities, entity-entity graphs and the like it is to be appreciated by the skilled person that the details of the present disclosure are applicable as the application demands to any other type of entity, information, data informatics fields and the like.

By way of example, details of the present disclosure will now be described, by way of example only but is not limited to, by way of reference to GNN models and Graph Convolutional Neural Networks (GCNN). It is to be appreciated by the skilled person that other GNN and/or neural network (NN) structures, and/or combinations thereof may be applied without loss of generality to the present invention as the application demands. The training techniques and resulting GNN model according to the invention may be based on, by way of example only but is not limited to, GCNN which are modified to include and learn attention weights that allow a robust GNN model for prediction tasks such as, by way of example only but is not limited to, relationship prediction to be efficiently generated and/or trained using uncertain or noisy graph datasets. An uncertain or noisy graph dataset may comprise or represent data representative of an entity-entity graph or a graph of facts where, by way of example only but is not limited to, the probability of a relationship between entities is uncertain; the probability of a plurality of relationship edges is uncertain; there is an uncertainty in the truthfulness or correctness of the relationships between entities. That is, there is informational "noise" in the entity-entity graph that may adversely affect the training of any machine learning (ML) technique such as neural networks. Causes of uncertainty or noise in entity-entity graphs may include, by way of example only but is not limited to, unreliable data sources; automatically curated data sources; automatically generated entity-entity graphs from automatically curated data sources; relationship extraction algorithms and/or processes being inaccurate or ill suited to entity and relationship extraction; ill equipped manual curation; poor natural language processing or optical character recognition algorithms for corpus of literature, patents and the like; multiple meanings given to the same entity and/or relationship; any other source of unreliability, uncertainty or noise in entity and relationship curation and extraction and the like.

Such uncertain or noisy entity-entity graph data sources may include relationship edges between entities that have uncertain relationships. Such relationship edges may be referred to as uncertain relationship edges. An uncertain or "noisy" relationship edge may comprise or represent a relationship edge between entity nodes of an entity-entity graph in which the relationship associated with the relationship edge is uncertain, incorrect, false or irrelevant. Examples of an uncertain relationship edge may include, by way of example only but is not limited to, probability of an edge or relationship edge being uncertain; a relationship edge with an uncertain relationships, a relationship edge with an irrelevant relationship, a relationship edge with an incorrect relationship, or any other relationship edge in which the relationship between entity nodes is unknown, false and the like. Causes of uncertainty or noise in relationship edges or relationships may include, by way of example only but is not limited to, unreliable data sources; automatically curated data sources; automatically generated entity-entity graphs from automatically curated data sources; relationship extraction algorithms and/or processes being inaccurate or ill suited to entity and relationship extraction; ill equipped manual curation; multiple meanings given to the same entity and/or relationship; any other source of unreliability, uncertainty or noise in entity and relationship curation and extraction and the like.

The attention weights are assigned to each edge of at least a portion of the graph dataset (or entity-entity graph) that is used to train the GNN model according to the invention. The resulting GNN model with learned attention weights has significant performance gains over other GNN models trained on the same uncertain or noisy entity-entity graph dataset. A GNN model based on a modified GCNN technique by including an attention weight for each relationship edge (also referred to as connection or link) of the entity-entity graph to reliably acquire an accurate posterior in a noisy link environment. The improved results of the modified GCNN technique and resulting GNN model are demonstrated herein using synthetic datasets, public datasets, and a large proprietary dataset derived from a mix of noisy and clean data sources. As the primary application of the modified GCNN technique and GNN graph model is towards prediction algorithms leveraging unstructured data, these techniques and models are further used to incorporate textual information into the GCNN representation to recover information that could be lost during a noisy relation inference or entity grounding step.

The below described system(s), apparatus and method(s) describe how to, by way of example only but is not limited to, efficiently increase the robustness of the GCNN technique to generate an accurate GNN model for prediction/classification problems in light of large noisy graph datasets during training and in decision directed mode (test or prediction mode). This is achieved by introducing an additional attention weight to each relationship link over an relationship edge between entities of an entity-entity knowledge graph. The entity-entity knowledge graph includes a plurality of entity nodes in which each entity node is connected to another entity node of the plurality of entity nodes by a relationship edge. The generated GNN model using the modified GCNN technique is capable of indirectly or explicitly filtering noisy or incorrect connections of a entity-entity knowledge graph, which may be generated from a database of facts or information such as, by way of example only but not limited to, a large-scale database, a corpus of information, literature, text and the like. New relationship connections between entity-entity nodes and accuracy of current relationship connections of the entity-entity knowledge graph may be determined by training the GCNN on the entity-entity knowledge graph to generate an embedding/representation of the entity-entity graph in the form of a graph model. Training the GCNN includes updating the weights of the GNN model including the attention weights by minimising a modified GCNN loss function with respect to an embedding and/or relationship scores associated with at least a portion of the entity-entity graph. The attention weights are learned by the modified GCNN technique during training of the GNN model by using the modified GCNN loss function and provide an indication of the relevancy of each relationship connection between entity nodes of the entity-entity relationship graph. The GNN model uses the attention weights during prediction tasks in which the attention weights are adapted/updated to suppress uncertain relationship edges of the entity-entity graph, which results in improved and/or robust predictions in light of uncertain and/or noisy graph datasets. The attention weights may be used to determine the relevancy of connections between entities. The attention weights may be read from the resulting GNN model and used to filter the original entity-entity relationship graph by weighting each relationship edge with the trained corresponding attention weight. The filtered entity-entity graph may be used to train another GNN model and/or update the trained GNN model.

Although details of the present disclosure are described, by way of example only but is not limited to, by way of reference to GNN models using GCNN, it is to be appreciated by the skilled person that other GNN and/or NN structures, and/or combinations thereof may be applied without loss of generality to the present invention as the application demands. For example, one or more neural network structures may be used to train a GNN to generate a trained GNN model based on an entity-entity graph dataset. The trained GNN model being for use, by way of example only but not limited to, link prediction problems and the like. NNs may comprise or represent one or more of a combination of neural network hidden layers, algorithms, structures and the like that can be trained to generate a GNN model associated with predicting links or relationships between one or more entities of the entity-entity graph from which the GNN model is generated. The GNN model may be applied to, by way of example only but is not limited to, link-prediction, relationship inference, relationship extraction, drug discovery, identification, and optimization and other tasks, objectives and/or problems in related data informatics, chem(o)informatics and/or bioinformatics fields.

Examples of NNs or NN structures that may be used by the invention as described herein may include or be based on, by way of example only but not limited to, at least one or more neural network structures from the group of: artificial NNs (ANNs); deep NNs; deep learning; deep learning ANNs; deep belief networks; deep Boltzmann machines; hierarchical temporal memory; rule-based machine learning; feedforward NNs; Long-Short-Term-Memory NNs (LSTM NNs); recursive NNs (RNNs); Convolutional NNs (CNNs); graph CNNs (GCNNs); autoencoder NNs; stacked Auto-Encoders; reinforcement learning (RL) algorithms and networks; extreme learning machines; logic learning machines; self-organizing maps; other ANN structures, techniques or connectionist systems/computing systems inspired by the biological neural networks that constitute animal brains and capable of learning or generating a model based on data representative of labelled and/or unlabelled graph datasets; any NN or NN algorithm/method that can be trained on data representative of labelled and/or unlabelled entity-entity graph datasets to generate a trained graph NN model associated with the labelled and/or unlabelled dataset; any other NN structure or technique capable of learning or generating a graph NN model based on learning data representations from data representative of labelled and/or unlabelled graph-based datasets and the like; any other NN structure suitable for use with graph NNs and/or data representative of entity-entity graph datasets and the like; and/or combinations thereof, modifications thereof and/or as described herein.

FIG. 1a is a schematic diagram illustrating an example graph neural network system 100 according to the invention. The system 100 may be configured to initially train a GNN model based on an entity-entity graph G 102. The system 100 may also be configured to use the trained GNN for prediction tasks such as, by way of example only but not limited to, link prediction, relationship inference, and/or relationship prediction. In training mode or during training of the GNN model, the system 100 receives or ingests data representative of at least a portion of an entity-entity graph 102 (e.g. G), which is input to an encoding network 104 (or encoding neural network) of the GNN model. The data representative of an entity-entity graph G 102 may include, by way of example only but is not limited to, an adjacency matrix or matrices describing the relationship between entity nodes of the graph, entity triples including data representative of a first entity node, a second entity node and a relationship therebetween, rules and/or actions in relation to including and/or excluding relationships, entity nodes or node pairs, and/or any other data capable or required for representing the entity-entity graph.

The encoding network 104 is configured to generate an embedding based on data representative of the portion of entity-entity relationship graph 102 that is ingested. The embedding is input to a scoring network 106 of the GNN model that may be configured to generate a relationship score in relation to each entity-entity relationship of the entity-entity graph G 102. Each relationship score (or prediction score) for a first and second entity and a relationship is an indication of the likelihood of the first entity being connected by a relationship edge to the second entity in relation to that relationship. The embedding generated may include an embedding of the entity nodes of the corresponding portion of the entity-entity graph, an embedding of the relationship edges and/or relationships. For example, the embedding may be based on data representative of one or more from the group of: at least a portion of the entity-entity graph for the GNN model; the entity-entity graph for the GNN model; one or more rules defining actions in relation to relationship edges; one or more rules defining actions in relation to entity nodes; one or more rules for including or excluding certain relationship edges or entity nodes; additional data for representing relationship edges/links or entities (e.g. chemical, compound, or molecular features for entities); data representative of rules or actions describing which entities may be linked or connected to other entities and the like.

The encoding network 104 of the GNN model is configured to generate an embedding that includes an attention weight assigned to each relationship edge of at least the portion of the entity-entity graph that is ingested. The attention weights are configured to indicate the relevancy of each corresponding relationship edge between entity nodes of the entity-entity graph and assist the GNN model in relationship prediction. The attention weights are learned by the GNN model during training on the entity-entity graph dataset.

During training of the GNN model, an updating or training module 108 may update the weights of the encoding network 104 including the attention weights and/or also the weights of the scoring network 106 of the GNN model by minimising a loss function in relation to the embedding and relationship scores. For example, the encoding network 104 may be based on, by way of example only, a GCNN in which the embedding is modified to include the attention weights and the GCNN loss function may be modified to include an attention loss function associated with the attention weights. The updating or training module may be configured to update the encoding network and/or the scoring network of the GNN model including the attention weights based on, by way of example only but is not limited to, stochastic gradient descent type algorithms, back propagation, and/or any other minimisation technique suitable for updating the encoding network and/or scoring network of the GNN model, modifications, and/or combinations thereof.

The updating or training module 108 may also include a determination mechanism for identifying when the GNN model has been validly trained. This may be based on, by way of example only but is not limited to, the number of training iterations that have been performed using the portion of the entity-entity graph, convergence of the weights of the encoding network and/or scoring network to within an error tolerance; or any other method or algorithm/technique for determining when a neural network system has been trained. If it is determined that the GNN model has not been validly trained, then the process repeats and the encoding network 104 re-ingests the entity-entity graph dataset to generate another embedding, which is passed to the scoring network 106 for generating relationship scores for use by the update or training module 108 for updating the weights of the encoding network 104 including the attention weights and/or the weights of the scoring network 106. This repeats until it is determined that the GNN model has been validly trained.

Although the GNN model with attention weights is described as being based on, by way of example only but is not limited to, a GCNN, it is to be appreciated by the skilled person that the GNN model with attention weights may be based on one or more neural networks from the group of: one or more artificial NNs; one or more feedforward NNs; one or more recursive NNs; one or more LSTMs, one or more Convolutional NNs; graph NNs; graph CNNs; autoencoder NNs; one or more other neural networks capable of being trained based on data representative of the entity-entity graph; combinations thereof, modifications thereof, and/or as described herein.

The encoding network (or encoder) may be based on any suitable neural network that is capable of generating one or more embeddings of at least a portion of the entity-entity graph. At the end of the encoding process (output of the encoding network), each entity of at least the portion of the entity-entity graph may be represented, by way of example only but is not limited to, an embedding vector (e.g. an N-dimensional embedding vector). As the choice of scoring network (or decoder) can be considered independently of the encoding system/network, a variety of methods from, by way of example only but is not limited to, tensor factorization can be employed, including DistMult, TransE, ComplEx, Rescal, and/or other suitable scoring/prediction neural networks, as the choice can be made independently of embedding framework.

Figure 1B:
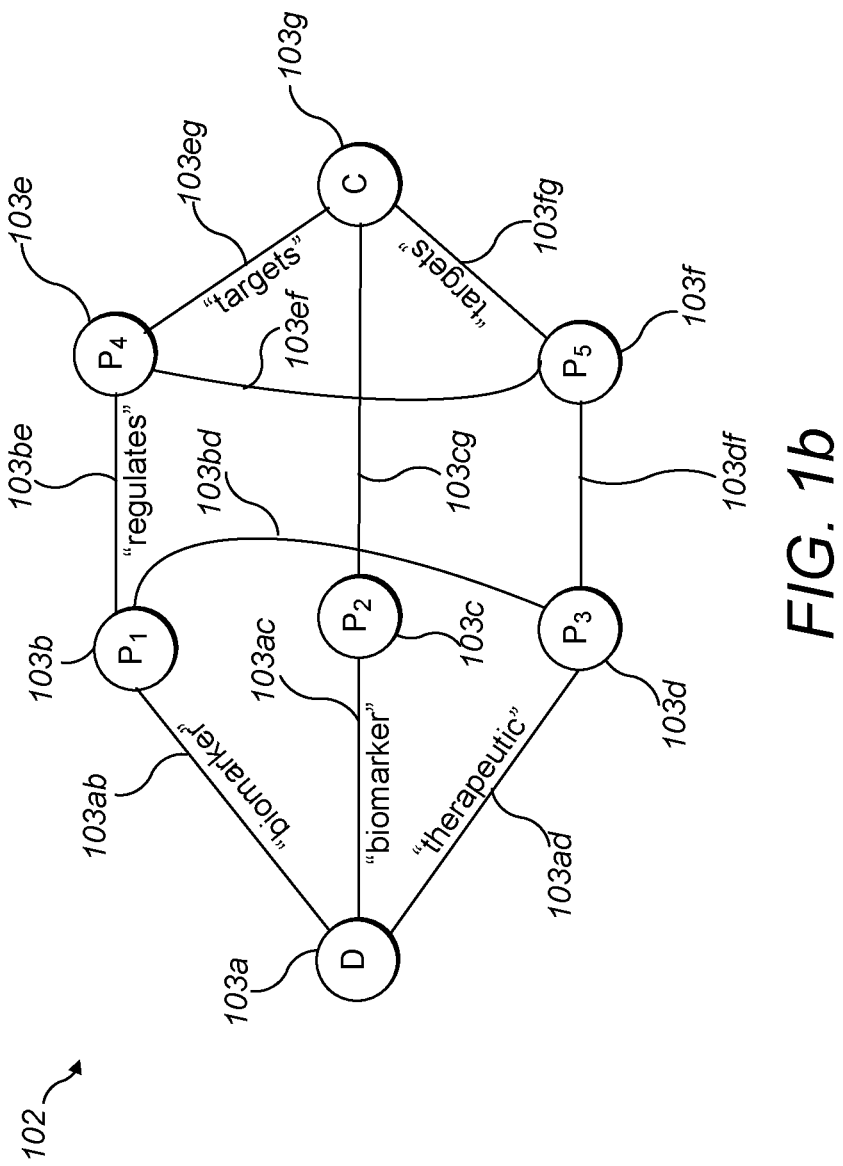
FIG. 1b is a schematic diagram illustrating an example entity-entity graph for input to a GNN model according to the invention.

FIG. 1b is a schematic illustration of a simple example entity-entity graph 102 in the biological field. In this example, the entity-entity graph includes data representative of entities and/or relationships from the group of: disease (D); compound/drug (C); and protein (P). Although only several types of entities are described in this example, this is for simplicity and it is to be appreciated by the skilled person that any entity from the group of: disease; compound/drug; protein; biological entity; pathway; biological process; cell-line; cell-type; symptom; clinical trials, any other biomedical concept; or any other entity as described herein or any other entity with at least an entity-entity relationship to another entity may be used as the application demands in the entity-entity graph. Referring to FIG. 1b, the entity-entity graph 102 is a knowledge graph that includes a plurality of entity nodes 103a-103g in which each of the entity nodes 103a-103g are connected to another entity nodes 103a-103g of the plurality of entity nodes by relationship edges 103ad, 103ab, 103be, 103cf, 103df, 103eg, 103fg.

The entity-entity graph G 102 may also be represented by a plurality of graph triples e=(s, r, o)∈G that relates a subject entity node s through a relation edge r to an object entity node o of the knowledge graph G 102. The entity-entity relationship graph 102 may be derived from a corpus of biological information, literature, patents, text, databases of facts and relationships (e.g. large-scale databases), the Internet, or any other suitable information source of data including two or more entities and one or more relationships connecting the entities. Any entity-entity relationship graph may be formed using, by way of example only but not limited to, based on any entity type of one or more entities associated with news; entertainment; email; social networks; communication networks; data informatics fields, chem(o)informatics fields, bioinformatics field(s), biological networks and any other information source and the like.

For biological networks or graphs, each entity node in an entity-entity relationship knowledge graph may represent or comprise, by way of example only but is not limited to, any entity from the group of: disease; compound/drug; protein; biological entity; or any other entity with at least an entity-entity relationship to another entity in the entity-entity relationship graph. In the example of FIG. 1b, the entity-entity relationship graph 102 is based on an example disease, protein, compound entity-entity relationship graph. The entity-entity relationship graph 102 includes a protein-protein interaction graph represented by a plurality of protein entity nodes 103b-103f, which in this example includes protein entity nodes $P_1$, $P_2$, $P_3$, $P_4$, and $P_5$. Each of the protein entity nodes 103b-103f is connected by one or more protein-protein relationship edges 103be, 103cg, 103bd and 103ef to another of the protein entity nodes 103b-103f. For example, protein entity node $P_1$ 103b is connected to protein entity node $P_4$ 103e by relationship edge 103be indicating $P_1$ "regulates" $P_4$, which may be represented by graph triple ($P_1$, "regulates", $P_4$)∈G; protein entity node $P_1$ 103b is connected to protein entity node $P_3$ 103d by relationship edge 103bd, which may be represented by graph triple ($P_1$, relationship edge 103bd, $P_3$)∈G; protein entity node $P_4$ 103e is connected to protein entity node $P_5$ 103f by relationship edge 103ef, which may be represented by graph triple ($P_4$, relationship edge 103ef, $P_5$)∈G; and protein entity node $P_3$ 103d is connected to protein entity node $P_5$ 103f by relationship edge 103df, which may be represented by graph triple ($P_3$, relationship edge 103df, $P_5$)∈G.

The entity-entity graph 102 also includes one or more disease entity nodes 103a, which in this example includes disease entity node D 103a. The disease entity node D 103a is connected to one or more of the protein entity nodes 103b-103f (e.g. $P_1$, $P_2$, $P_3$) by corresponding relationship edges 103ab, 103ac, and 103ad. For example, the disease entity node D 103a is connected to protein entity node $P_1$ by relationship edge 103ab, indicating $P_1$ is a "biomarker" of disease D, which may be represented by graph triple (D, "biomarker", $P_1$)∈G; the disease entity node D 103a is also connected to protein entity node $P_2$ by relationship edge 103ac indicating $P_2$ is a "biomarker" of disease D, which may be represented by graph triple (D, "biomarker", $P_2$)∈G; and the disease entity node D 103a is connected to protein entity node $P_3$ by relationship edge 103ad indicating $P_3$ is a "therapeutic" for disease D, which may be represented by graph triple (D, "biomarker", $P_3$)∈G. The entity-entity graph 102 also includes one or more compound/drug entity nodes 103g, which in this example includes compound entity node C 103g. The compound entity node C 103b is connected to one or more of the protein entity nodes 103b-103f (e.g. $P_2$, $P_4$ and $P_5$) by corresponding relationship edges 103cg, 103eg and 103fg. For example, the compound entity node C 103g is connected to protein entity node $P_2$ by relationship edge 103cg, which may be represented by graph triple (C, relationship edge 103cg, $P_2$)∈G; the compound entity node C 103g is connected to protein entity node $P_4$ by relationship edge 103eg indicating $P_4$ is a "target" of compound C, which may be represented by graph triple (C, "target", $P_4$)∈G; and the compound entity node C 103g is connected to protein entity node $P_5$ by relationship edge 103fg indicating $P_5$ is a "target" of compound C, which may be represented by graph triple (C, "target", $P_5$)∈G. The entity-entity relationship graph 102 forms a graph dataset for use in generating a GNN model for prediction tasks, such as by way of example only but is not limited to, link prediction and/or relationship inference, classification and the like.

Neural networks may be used to generate graph models for predicting/classifying problems associated with training datasets by determining embeddings or a latent space associated with the training dataset and using a loss function to update weights of hidden layers of the GNN model (e.g. the encoding network 104 and scoring network 106). For graph based datasets, graph-based neural networks, such as GCNN technique(s) and the like may be used to determine entity node and relationship edge (or context) embeddings for relationship inference. The encoding network 104 may build up or be trained to generate a relationship embedding vocabulary or library representing each of the unique relationships in the ingested entity-entity graph. Neural network techniques may be used to generate an embedding of each entity node in the entity-entity relationship graph 102 and also an embedding of each relationship between entity nodes using, by way of example only but not limited to, neural network encoding and scoring networks 104 and 106. The embedding of each entity node of the graph 102 may be represented by an N-dimensional vector and the embedding of each relationship between entity nodes of graph 102 may also be represented by an N-dimensional vector.

For example, conventional GCNNs may be used to generate an embedding of graph 102 by using convolutional graph neural network operations for embedding each entity node as an N-dimensional vector using relationship scoring. The convolutional operation is briefly outlined below and described in terms of building or generating layers of embeddings (or convolutions of embeddings of the entity nodes). Essentially, each embedding layer builds upon the previous embedding layer. For example, an embedding for disease entity node D 103a for a layer l+1 may be represented, by way of example only but is not limited to, an N-dimensional vector $v_D^{l+1}=\sigma(v_D^{l+1}+\Sigma_{(D,r,P)\in G} W_r^l v_P^l)$, where $\sigma(\bullet)$ as an activation function (e.g. ReLu), $W_r^l$ is an N×N dimensional adjacency matrix for layer l representing relationships associated with relation index r∈R between entity node D and protein node P in graph G 102, R being the set of relations, $v_D^l$ is an N-dimensional vector embedding of the disease entity node for the previous layer l, $v_P^l$ is an N-dimensional vector embedding of protein entity node P connected by relation r to disease entity node D 103a for previous layer l, or the protein entity node P that satisfies the graph triple (P, r, D)∈G. Each of the embeddings for the other entity nodes P and C 103b-103g may be calculated in a similar fashion. For example, an embedding for compound entity node C 103g for the first layer may be represented as an N-dimensional vector $v_C^{l+1}=\sigma(v_C^{l+1}+\Sigma_{(P,r,C)\in G} W_r^l v_P^l)$ where $v_C^l$ is an N-dimensional vector embedding of the compound entity node for the previous layer, $v_P^l$ is an N-dimensional vector embedding of protein entity node P connected by relation with relation index r∈R to compound entity node 103g for layer l, or the protein entity node P that satisfies the graph triple (P, r, C)∈G. Similar embeddings for each of the protein entity nodes 103b-103f may be formed.

This layering of the embeddings may be repeated a number of L times. Thus, as the number of layers increases, each embedding for each entity node includes more information from entity nodes and/or relationships further away from that entity node. This additional information is used by the encoding network 104 in an attempt to generate a richer set of embeddings for the entity nodes and/or relationships therebetween. However, this assumes that the relationships between entity nodes in the entity-entity relationship graph are all correct.

Conventional graph-based neural network techniques such as the above describe conventional GCNN technique are essentially unable to ignore or remove noise or uncertain relationship edges from less useful relationship edges or entity nodes in the knowledge graph 102, which have a negative impact on the performance of the resulting graph output by the graph-based neural network technique (e.g. GCNN technique). It has been found that this is because such techniques may inadvertently sample: i) the wrong edges; or ii) cannot handle incorrect edges, every time a representation of the knowledge graph 102 is built by the graph-based neural network technique (e.g. GCNN technique). Effectively, the information associated with uncertain relationship edges accumulates and causes the encoding network 104 and scoring network 106 of the GNN model to learn incorrect relationships and facts, which negatively impacts prediction performance. Thus, such graph-based neural network techniques cannot efficiently or robustly: a) learn new relationship connections between entity-entity nodes in the graph 102; and b) determine the accuracy of current relationship connections of the entity-entity relationship graph 102.

As the entity-entity relationship graph 102 forms a basis or a training knowledge graph dataset for use by a graph-based technique (e.g. a GCNN technique) according to the invention for learning or determining: a) new relationship connections between entity-entity nodes in the graph; and b) the accuracy of current relationship connections of the entity-entity relationship graph. The entity-entity relationship graph may be input as a training dataset for training a neural network technique to generate an GNN model for predicting or classifying entity-entity relations associated with the entity-entity knowledge graph.

According to the invention, an attention weight may be assigned to each relationship edge of the entity-entity graph 102 that is used to train the GNN model and the GCNN technique is used to train the GNN model. The loss function of the GCNN technique, or any other graph-based neural network technique, is modified to form a modified GCNN loss function with an additional attention weight cost function. The modified loss function may be minimised based on the embedding and/or the relationship scores of a scoring network 106 and used to update the encoding network 104 including the attention weights. The attention weights are included into the embedding in such a fashion that they indicate the relevancy of each relationship connection between entity nodes of the entity-entity relationship graph 102. A set of attention weights are learned by the GNN model based on, by way of example only, the GCNN technique being trained on an embedding of the entity-entity relationship graph 102 with the assigned attention weights.

When the GCNN technique is used, the addition of 1) attention weights to a GCNN loss function assists the GCNN to determine suitable node and relationship or context embeddings by removing the noise of less useful relationship edges in the entity-entity knowledge graph 102 that have a negative impact and avoids sampling the wrong or incorrect edges every time an embedding representation of the graph 102 is built. The attention weights allow incorrect facts to be identified, and thus the GNN model can take these incorrect facts into account when making predictions (e.g. the attention weights can suppress incorrect facts); in addition, the attention weights may be used to explicitly filter the entity-entity knowledge graph 102 by removing edges of the.

In a simple example, disease entity node D 103a may be connected to protein entity nodes $P_1$ and $P_2$ 103b and 103c by relationship edges 103ab and 103ac, which have the same relationship "biomarker", respectively. Thus, these entity-entity nodes pairs may be associated with "biomarker" relation $r \in R$. The conventional GCNN embedding for disease entity node D 103a with "biomarker" relation r for a layer/may be represented as an N-dimensional vector $h_D^{l+1} = \sigma(h_D^l + W_r^l h_{P_1}^l + W_r^l h_{P_2}^l)$, where $\sigma(\cdot)$ as an activation function (e.g. ReLu), $W_r^l$ is an N×N dimensional adjacency matrix for "biomarker" relation $r \in R$, R being the set of relations, $h_D^l$ is an N-dimensional vector embedding of the disease entity node for the previous layer, $h_{P_1}^l$ is an N-dimensional vector embedding of protein entity node $P_1$ 103b for the previous layer connected by relation $r \in R$ to disease entity node 103a, or the protein entity node $P_1$ that satisfies the graph triple $(P_1, r, D) \in G$, $h_{P_2}^l$ is an N-dimensional vector embedding of protein entity node $P_2$ 103c for the previous layer connected by "biomarker" relation $r \in R$ to disease entity node 103a, or the protein entity node $P_2$ 103c that satisfies the graph triple $(P_2, r, D) \in G$.

According to the invention, the conventional embedding is modified to include scalar attention weights $\alpha_{r,D,P}$ that are associated with the connection with "biomarker" relation r between disease entity node D 103a and the corresponding protein entity nodes $P_1$ and $P_2$ 103b and 103c. For example, the convention embedding may be modified to form an embedding including attention weights according to the invention for disease entity node D 103a with "biomarker" relation r for a layer l+1 which may be represented as an N-dimensional vector $h_D^{l+1} = \sigma(h_D^l + \alpha_{r,D,P_1} W_r^l h_{P_1}^l + \alpha_{r,D,P_2} W_r^l h_{P_2}^l)$, where $\alpha_{r,D,P_1}$ and $\alpha_{r,D,P_2}$ are the scalar attention weights associated with the connection with "biomarker" relation r between disease entity node D 103a and the corresponding protein entity nodes $P_1$ and $P_2$ 103b and 103c. Similar embeddings for each of the protein entity nodes 103b-103f and compound entity node 103g may also be formed. The GCNN may be used to train or generate a GNN model embodying the embeddings of the disease, compounds and protein entity nodes including the attention weights, in which the attention weights are updated by minimising a loss function (e.g. using stochastic gradient descent based algorithms and the like) associated with the attention weights.

The resulting GNN model may be used to predict relationships between entity nodes of the graph 102 and also the learned attention weights may be output and used to filter the entity-entity knowledge graph 102 of irrelevant relationships. For example, representations of two or more entities may be input to the graph model, which predicts whether there is a relationship between the entities by outputting an indication or relationship score of the likelihood of a relationship existing between the entities. For example, the two or more entities may be entity nodes in the graph 102.

Figure 1C:
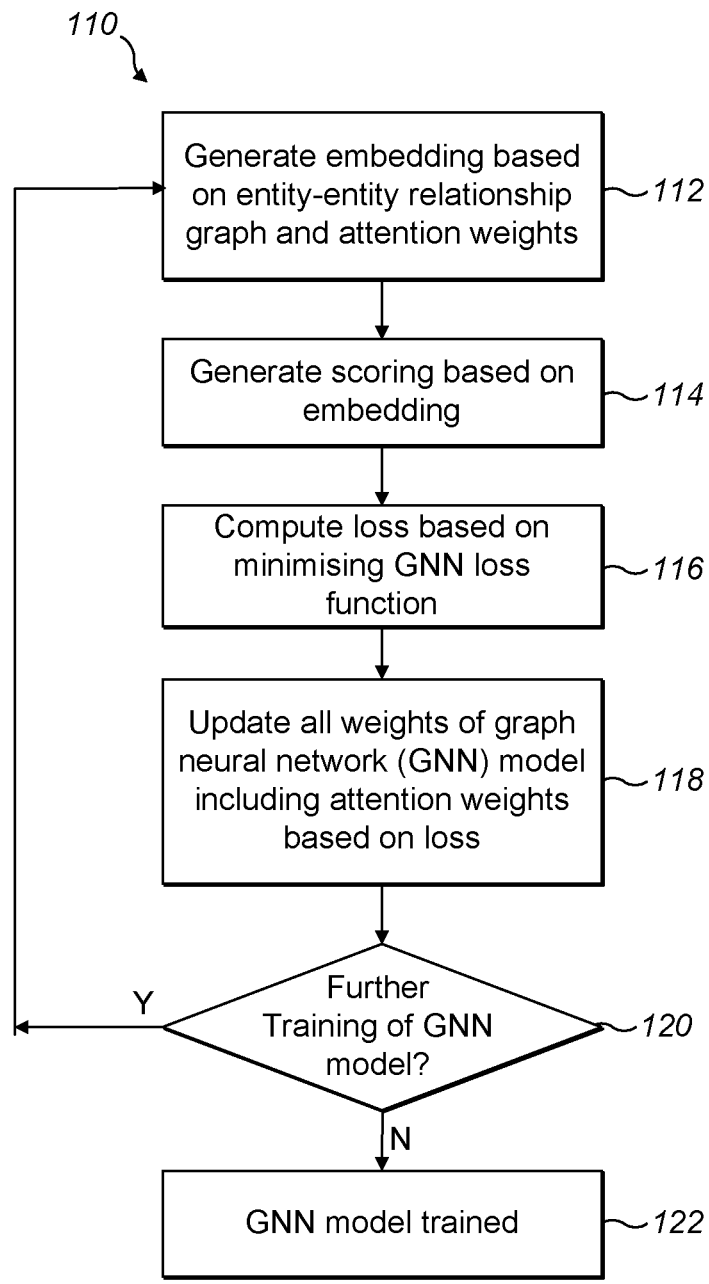
FIG. 1c is a flow diagram illustrating an example process for training a GNN model according to the invention.

FIG. 1c is a flow diagram illustrating an example process 110 for generating a GNN model for prediction relationships and the like based on an entity-entity relationship graph according to the invention. The entity-entity relationship graph includes a plurality of entity nodes in which each entity node is connected to one or more entity nodes of the plurality of entity nodes by a relationship edge. The process 110 includes the following steps of: In step 112, generating an embedding based on data representative of at least a portion of the entity-entity graph for the GNN model, where the embedding includes an attention weight assigned to each relationship edge of at least the portion of the entity-entity graph. The attention weights indicate the relevancy of each corresponding relationship edge between entity nodes of the entity-entity graph and assist the GNN model in relationship prediction. The GNN may be based, by way of example only but not limited to, a GCNN technique. In step 114, generating one or more relationship scores based on data representative of one or more embedding(s) associated with the portion of entity-entity graph. In step 116, a loss is computed based on minimising a GNN loss function. For example, if the GNN model is based on the GCNN technique, then a GCNN loss function may be minimised using stochastic gradient descent back-propagation algorithms. In step 118, updating the GNN model including the attention weights based on the computed loss by minimising the GNN loss function associated with at least the embedding. Additionally, the scoring network 106 of the GNN model may be updated including the attention weights based on the computed loss by minimising the GNN loss function based on at least the embedding and/or the relationship scores of the scoring network 106. The attention weights indicate the relevancy of each relationship connection between entity nodes of the entity-entity relationship graph.

In step 120, it is determined whether further training of the graph model is necessary, and if so (e.g. Y), then repeating step 112 of generating the embedding based on the entity-entity relationship graph and steps 114 to 118 in relation to scoring, computing the loss, and updating weights of the encoding network 104 including the attention weights and/or weights of the scoring network 106 of the GNN model. If it is determined that further training of the GNN model is not necessary (e.g. 'N'), i.e. the graph model has been validly trained or a maximum number of training iterations have occurred etc., then the process proceeds to step 122, in which a trained GNN model is output for use in prediction tasks and the like.

The GNN model that is output may be used to predict link relationships between entities in the entity-entity relationship graph by inputting to the GNN representations of two or more entities and/or one or more relationships. The GNN may output one or more relationship scores indicating the likelihood that the two or more entities have the one or more relationships. For example, data representative of a first entity, a second entity and a relationship may be input to the GNN for predicting whether the first and second entity are related by the relationship. The GNN may output a relationship score associated with the relationship indicating whether the first and second entity have the relationship. The trained attention weights of the GNN model ensure that the GNN model may ignore incorrect or noisy connections within the graph that was used to train the GNN model, which enhances the robustness and prediction accuracy of the GNN.

Alternatively or additionally, the trained attention weights of the GNN model may be output for use as the application demands. The trained attention weights that are output may be used to filter the entity-entity relationship graph by weighting each edge with the corresponding trained attention weight. Filtering the entity-entity graph may further include removing a relationship edge from the entity-entity graph if the corresponding attention weight is below and/or equal to an attention threshold. The attention threshold may be predetermined or adjusted depending on the amount of perceived noise in the entity-entity graph. This may be used to improve the entity-entity relationship graph, which may in turn be used to further train another GNN model or even update the present trained GNN model. The GNN model may be further updated based on the filtered entity-entity relationship graph. The updated GNN model may be used to predict link relationships between entities in the filtered entity-entity relationship graph by inputting to the updated GNN model representations of two or more entities and/or one or more relationships; and receiving an indication of the likelihood of a link relationship existing between the two or more entities.

The trained GNN according to the invention may be used for predicting link relationships between entities in the filtered entity-entity relationship graph by inputting to the updated GNN model representations of two or more entities and/or one or more relationships. The updated GNN model may then output a relationship score, and thus an indication of the likelihood of a link relationship existing between the two or more entities may be received. Alternatively, the trained GNN model with attention weights does not require re-training with a filtered entity-entity graph as the attention weights have been configured to suppress uncertain relationship edges. Thus, the trained GNN model may be used for predicting link relationships between entities by inputting to the GNN model representations of two or more entities and/or one or more relationships, in which an indication or relationship score(s) of the likelihood of one or more link relationship(s) existing between the two or more entities may be output and/or received.

Step 116 may further include minimising the GNN loss function, $\mathcal{L}(\bullet)$, by: assigning an attention weight, $\alpha_{r,i,j}$, to each relationship edge of the entity-entity graph, wherein $\alpha_{r,i,j}$ is the attention weight associated with the connection between entity node i and entity node j with relation index r of the plurality of relationships associated with the entity-entity graph; modifying the loss function by adding an attention loss function, $\mathcal{L}_{att}(\hat{\Lambda})$, associated with the set of attention weights $\hat{\Lambda}=\{\alpha_{r,i,j}\}$ to the loss function; and minimising the modified loss function, $\mathcal{L}_{mod}(\bullet)$, with respect to the weights of the GNN model including the attention weights; where the modified loss function is $\mathcal{L}_{mod}(\bullet) = \mathcal{L}(\bullet) + \mathcal{L}_{att}(\hat{\Lambda})$.

In one example, the GCNN technique may be used and so a modified GCNN loss function may be formed based on $\mathcal{L}_{GCNNmod}(\bullet) = \mathcal{L}_{GCNN}(\bullet) + \mathcal{L}_{att}(\hat{\Lambda})$. Modifying the GCNN loss function $\mathcal{L}_{GCNN}(\bullet)$ may further include adding an $l^1$-norm based on $\mathcal{L}_{att} = \lambda \Sigma_{r \in \mathcal{R}} \Sigma_i \Sigma_{j \in \mathcal{N}_i} |\alpha'_{r,i,j}|$ where $\lambda \in \mathbb{R}$ is a hyperparameter representing a cost weighting factor. The attention weights may be further regularised in which each of the updated attention weights $\alpha_{r,i,j}$, are set to a normalised attention weight $\alpha'_{r,i,j}$ based on:

$$\alpha'_{r,i,j} = \frac{1}{\Sigma_r \Sigma_j |\alpha_{r,i,j}|} |\alpha_{r,i,j}|,$$

where the attention weight $\alpha_{r,i,j}$ is initially set to 1 and $\alpha'_{r,i,j} = 1/|\mathcal{N}_i|$ for all j prior to training the GNN model, which may be based on the GCNN technique.

In step 112, generating the embedding of the entity-entity relationship graph may further include representing the embedding for each entity node i of the entity-entity relationship graph and layer l+1, for $0 \le l$, as an N-dimensional vector $h_i^{(l+1)}$ that is defined by: $h_i^{(l+1)} = \sigma(\Sigma_{r \in \mathcal{R}} \Sigma_{j \in \mathcal{N}_i^r} \alpha_{r,i,j} W_{j,r}^{(l)} h_j^{(l)} + b_i^{(l)})$, where r is a relation index of a relationship from the set of all relationships $\mathcal{R}$ associated with the relationship edges of the entity-entity graph, and j is the index of an entity node connecting to entity node i within $\mathcal{N}_i^r$, $\mathcal{N}_i^r$ the set of all nodes that connect to entity node i for relation index r, $\alpha_{r,i,j}$ is the attention weight associated with the connection between entity node i and entity node j for relation index r, $b_i^{(l)}$ is a node-specific layer-wise bias vector applied to the embedding $h_i^{(l+1)}$, $W_{j,r}^{(l)}$ is the associated relationship adjacency matrix for the l-th hidden layer associated with entity node i, and $\sigma(\bullet)$ is an activation function.

Figure 1D:
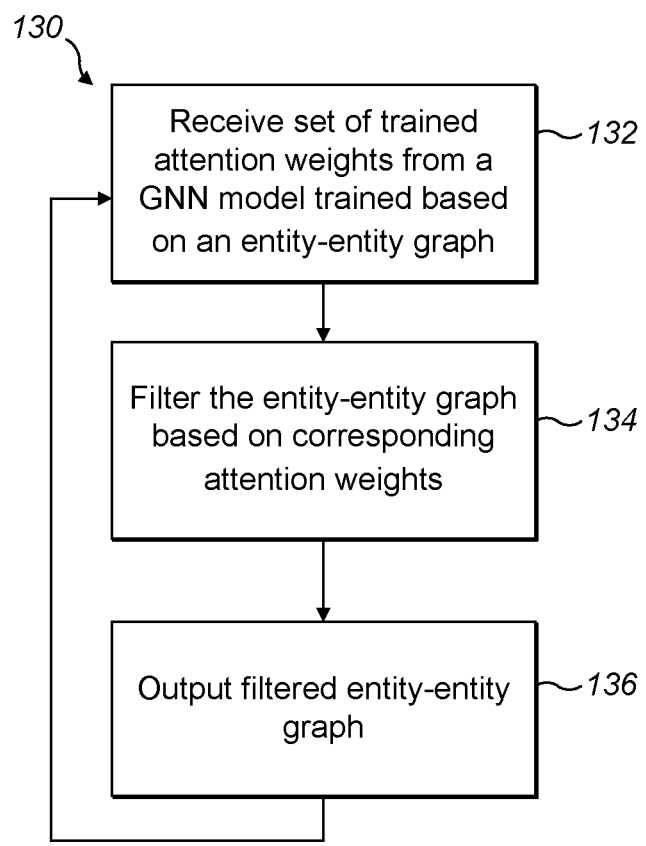
FIG. 1d is a flow diagram illustrating an example process for filtering an entity-entity graph according to the invention.

FIG. 1d is a flow diagram illustrating an example process 130 for filtering an entity-entity graph according to the invention. The entity-relationship graph includes a plurality of entity nodes in which each entity node is connected to one or more entity node of the plurality of entity nodes by a relationship edge. The entity-entity relationship graph or a portion thereof may be used to train a GNN model in which an attention weight is assigned to each relationship edge of the entity-entity graph or portion thereof. The process 130 further including the steps of: In step 132, receiving a set of attention weights from the GNN model, where the GNN model has been trained based on data representative of the entity-entity graph or a portion thereof with an attention weight assigned to each relationship edge of the entity-entity graph or a portion thereof in which the attention weights are updated during training and are indicative of the relevancy of each corresponding relationship edge between entity nodes of the entity-entity graph or portion thereof. In step 134, generating a filtered entity-entity relationship graph by weighting each edge with the corresponding trained attention weight. Filtering the entity-entity graph based on the trained attention weights may include removing those relationship edge(s) from the entity-entity graph or portion thereof having a corresponding trained attention weight that is below or equal to an attention relevancy threshold. Alternatively, filtering the entity-entity graph may include removing those relationship edge(s) from the entity-entity graph or portion thereof having a corresponding trained attention weight that is above or equal to another attention relevancy threshold. In step 136, the filtered entity-entity graph may be output. Additionally or alternatively, step 134 may further include identifying uncertain relationship edges in the entity-entity graph or portion thereof based on a set of attention weights retrieved from the trained GNN model associated with the entity-entity graph and an attention relevancy threshold. The identified uncertain relationship edges may be culled, removed, and/or rules may be derived defining actions for excluding the relationship edges, where the rules for part of the data representative of the entity-entity graph. Once a filtered entity-entity graph has been output, it may be used to update the GNN model based on the filtered entity-entity graph. Alternatively or additionally, the output filtered entity-entity graph may be used by a graph-based technique to generate or train another GNN model based on the filtered entity-entity graph.

Figure 1E:
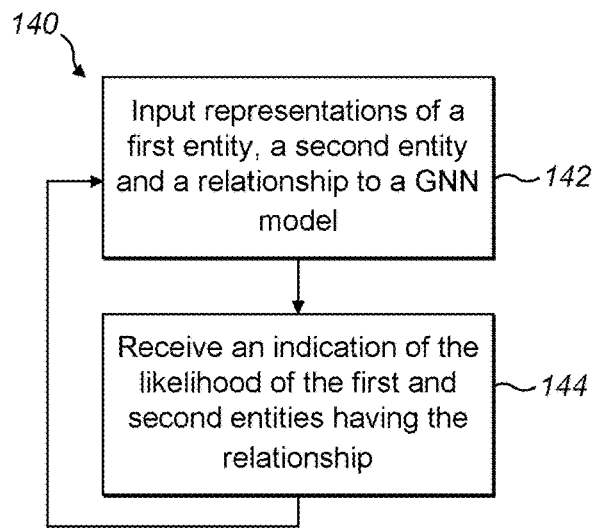
FIG. 1e is a flow diagram illustrating an example process for operating the GNN model according to the invention.

FIG. 1*e* is a flow diagram illustrating an example process 140 for operating or using a GNN model according to the invention or a GNN model obtained based on a filtered entity-entity graph according to the invention. The GNN model is trained for predicting relationships between entities in an entity-entity relationship graph, where the GNN model has been trained based on data representative of the entity-entity graph or portions thereof with an attention weight assigned to each relationship edge of the entity-entity graph or portions thereof in which the attention weights are updated during training and are indicative of the relevancy of each corresponding relationship edge between entity nodes of the entity-entity graph. The attention weights may assist the GNN model in predicting relationships by suppressing those one or more relationships that are uncertain relationships and/or are incorrect relationships (e.g. suppressing those entities nodes in the entity-entity graph with uncertain relationship edges). The steps of the process 140 may include: In step 142, inputting to the GNN model representations or data representative of a first entity, a second entity and a relationship. In step 144, receiving a relationship score in relation to the input relationship from the GNN model, the relationship score indicating the likelihood of the first and the second entity having the relationship. Although the relationship score may indicate, by way of example only but is not limited to, the likelihood of the first and the second entity having the relationship, it is to be appreciated by the skilled person that the relationship score may indicate, by way of example only but not limited to, one or more of a probability that the first and second entity have the relationship, a binary value indicating the first and second entity have or do not have the relationship, or any other value indicating whether the first and second entity have or do not have the relationship.

Step 142 may be modified to inputting to the graph model representations of two or more entities; and step 144 may be modified to receiving an indication of the likelihood of a relationship existing between the two or more entities.

Figure 1F:
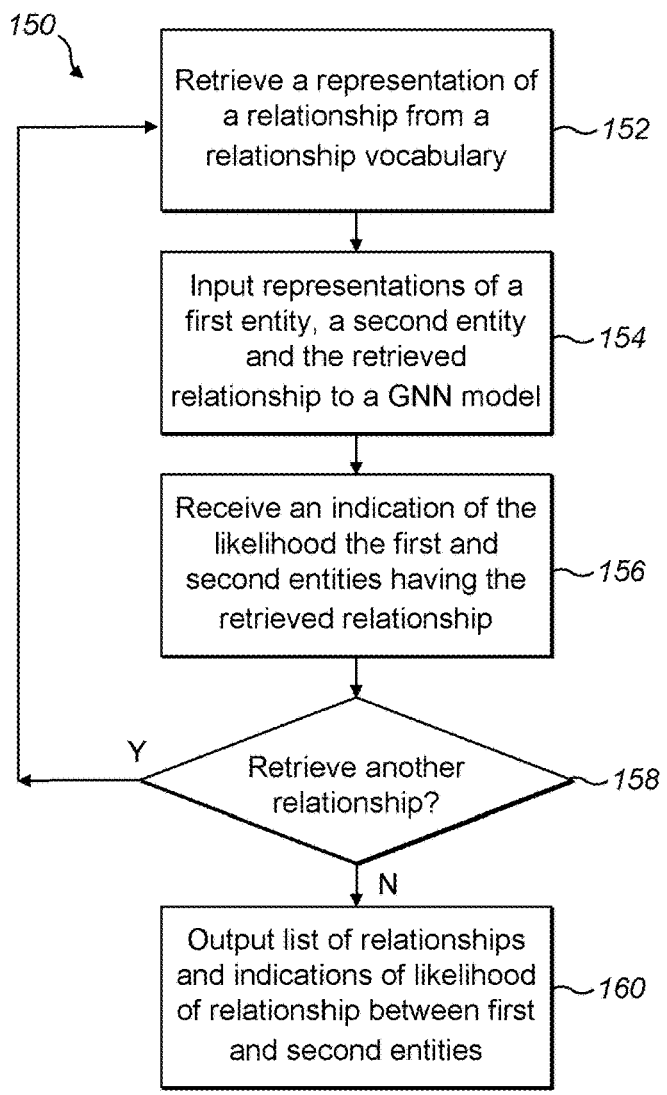
FIG. 1f is a flow diagram illustrating another example process for operating the GNN model according to the invention.

FIG. 1*f* is a flow diagram illustrating another example process 150 for operating or using a GNN model according to the invention or a GNN model obtained based on a filtered entity-entity graph according to the invention. The GNN model is trained for predicting relationships between entities in an entity-entity relationship graph, where the GNN model has been trained based on data representative of the entity-entity graph or portions thereof with an attention weight assigned to each relationship edge of the entity-entity graph or portions thereof in which the attention weights are updated during training and are indicative of the relevancy of each corresponding relationship edge between entity nodes of the entity-entity graph. The attention weights may assist the GNN model in predicting relationships by suppressing those one or more relationships that are uncertain relationships and/or are incorrect relationships. The steps of the process 150 may include: In step 152, retrieving a representation of a relationship from a relationship vocabulary, where the relationship vocabulary may include a plurality of relationship embeddings that are mapped to the corresponding relationships. The relationship embeddings may be mapped to a relationship or relation index, which identifies the corresponding relationship. In step 154, inputting to the GNN model representations or data representative of a first entity, a second entity and the retrieved relationship. In step 156, receiving a relationship score in relation to the input relationship from the GNN model, the relationship score indicating the likelihood of the first and the second entities having the retrieved relationship. In step 158, it is determined whether another relationship is to be retrieved. If another relationship is to be retrieved (e.g. 'Y'), then the process 150 proceeds to step 152. If another relation is not to be retrieved (e.g. 'N'), then the process 150 proceeds to step 160. In step 160, the GNN model or a wrapper to the GNN model outputs a list of retrieved relationships and corresponding relationship scores and/or indications of the likelihood of the retrieved relationship between the first and second entities. Although the relationship score may indicate, by way of example only but is not limited to, the likelihood of the first and the second entity having the relationship, it is to be appreciated by the skilled person that the relationship score may indicate, by way of example only but not limited to, one or more of a probability that the first and second entity have the relationship, a binary value indicating the first and second entity have or do not have the relationship, or any other value indicating whether the first and second entity have or do not have the relationship.

Although FIGS. 1*a*-1*f* describe generating, training and using a GNN model for filtering and/or predicting relationships using, by way of example but are not limited to, an example entity-entity relationship graph 102 and a GCNN technique it is to be appreciated by the skilled person that any entity-entity graph may be used as the application demands and any suitable NN technique may be used to train the GNN model for predicting relationships and the like as the application demands.

Details of the present disclosure will now be described, by way of example only but is not limited to, by way of reference to GNN models and GCNNs for generating and training the GNN model according to the invention based on general entity-entity relationship graphs. The general entity-entity graphs may be formed from any information source and/or database of facts and/or entity relationships and the like (e.g. large-scale databases of facts). In particular, the entity-entity relationship graph is assumed to be an undirected knowledge graph $\mathcal{G}$ described by a set of edges $\varepsilon$, with a plurality of edge triples $x=(s, r, o) \in \varepsilon$ each of which relates a subject entity node s through a relation edge with relation index r in the set of relations to an object entity node o of the knowledge graph $\mathcal{G}$.

Despite the fact that link prediction is an inherently graph-formulated task, learnable graph-based ML techniques or algorithms that are able to efficiently ingest a graph structure to perform prediction have arrived relatively recently. The interest in making predictions on graph-ingested data reached a peak after the initial successes of deep convolutional neural networks. The efforts to extend those extremely successful models to support graph data while still offering efficient transforms on neighbourhoods around nodes are typically divided into two classes of approaches. The first set of methods, referred to as spectral approaches bootstraps the insight that a convolution can be defined in the Fourier domain by computing operations on the Laplacian eigenbasis, and now provide methods for learning spatially-localized filters dependent on the graph structure. The second class of methods, non-spectral, define convolutions directly on the graph, but the challenge remains of offering an operation that is invariant to edge order and node degree. Approaches such as separating learned weights by node degree, extracting and normalizing a fixed number of nodes, or sampling through a recurrent architecture have found successful applications recently. However, in nearly all of these approaches, the weights of the graph model transform the features on the nodes of the graph, while a link weight is usually a function of the connectivity of that node of the graph.

To motivate the addition of a link weight in a conventional GCNN technique, observe that while a standard tensor factor model samples a training link once per training epoch, a conventional GCNN technique samples that training link whenever the subject or object entity is fetched, resulting in orders of magnitude more samplings of an incorrect edge. For the undirected graph $\mathcal{G}$ described by the set of edges $\mathcal{E}$, the given edge triple $x=(s, r, o) \in \varepsilon$ has the following probability of being sampled during training:

$$p_{tensor}(X = x) = \frac{1}{|\varepsilon|} p_{GCNN}(X = x) = \frac{|E_s|}{|\varepsilon|} + \frac{|E_o|}{|\varepsilon|}$$

Where $E_s$ is the set of all edge triples containing the subject entity s, and $E_o$ is the set of all edge triples containing the object entity o, and $|\varepsilon|$ refers to the number of edges in $\varepsilon$. Note that both individually are considerably larger than $1/|\varepsilon|$, and so is their sum. For comparison, the graph dataset FB15k-237 (i.e. this dataset contains knowledge base relation triples and textual mentions of Freebase entity pairs) has a median connectivity of 16 edges per node; therefore $p_{GCNN}/p_{tensor}$ results in a median edge sampled 32 times more often when calculating links using the conventional GCNN technique. Considering second-order neighbours within the conventional GCNN technique squares the number of needed connections, raising it to 512 times more samplings per epoch. For more densely-connected datasets or even more distant neighbour influences, this problem is further exacerbated. Possibly spurious links, therefore, have a profoundly greater influence on training a conventional GCNN technique for link prediction than in traditional tensor factor models. The modified GCNN technique aims to rectify this deficiency to efficiently generate robust graph models that are capable of overcoming noisy and/or incorrect connections within the training graph dataset.

Figure 2:
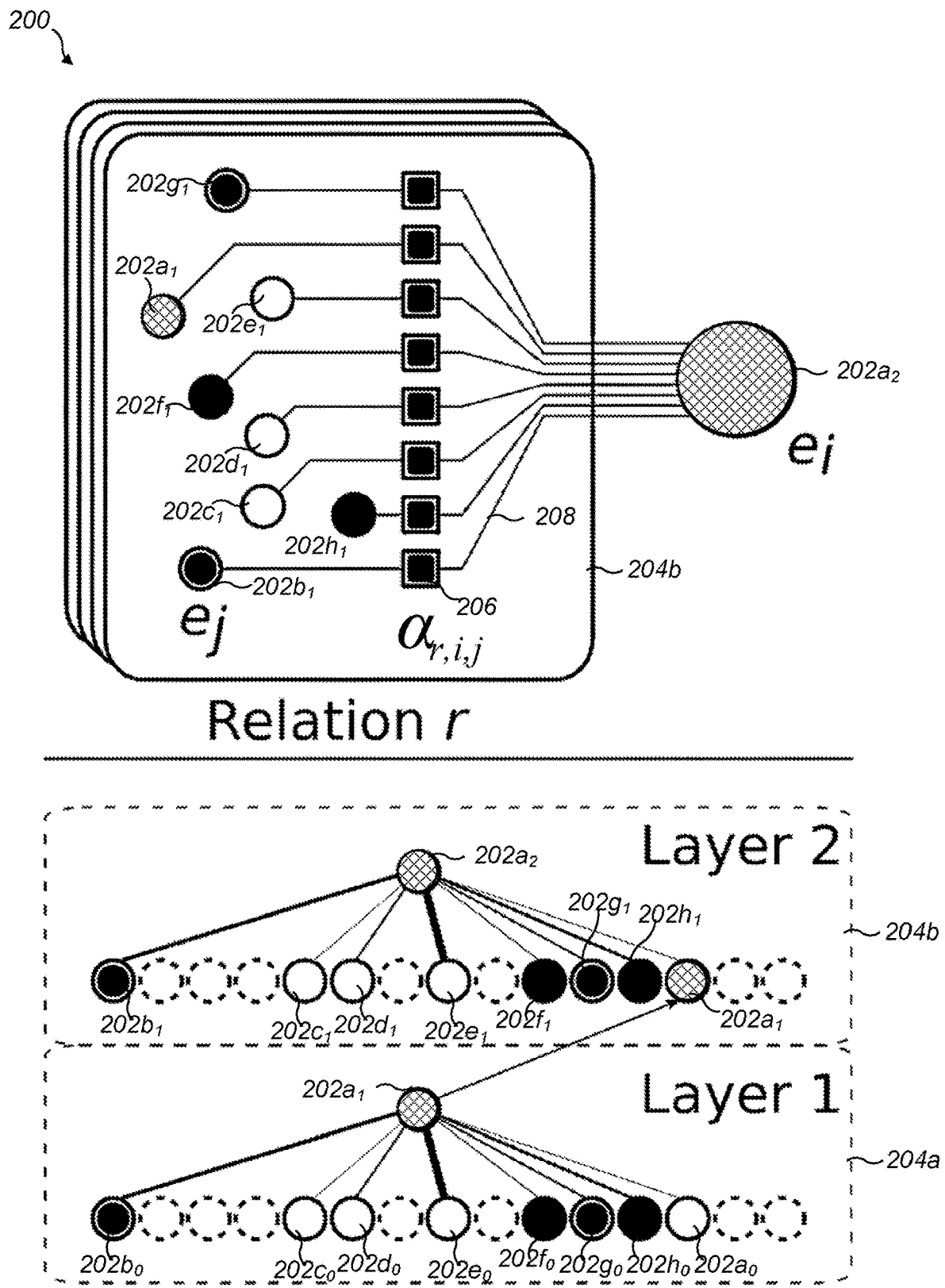
FIG. 2 is a schematic diagram illustrating a GNN model based on a graph convolution neural network structure according to the invention.

FIG. 2a is a schematic diagram illustrating an example modified GCNN 200 for an encoder network of a GNN model according to the invention. The entity-entity knowledge graph $\mathcal{G}$ includes a plurality of entity nodes each connected by relationship edges to one or more other entity nodes, each relationship edge having a relation with a relation index r from the set of all relations $\mathcal{R}$. During training of the GNN model based on the modified GCNN a number of embeddings of each entity node is generated in a multi-layer scenario. In this case, there are 2 layers 204a and 204b and for each layer each entity node is visited and an embedding of the entity node is generated based on the sum of input representations of previous embeddings of the entity nodes connected to it. For example, in FIG. 2a, the i-th entity node $e_i$ $202a_2$ in layer 204b is shown as being visited and an embedding of the i-th entity node $e_i$ $202a_2$ is generated based on the sum of the input representations of the embeddings of the entity nodes $202a_1$, $202b_1$, ..., $202h_1$ of layer 204a connected to it associated with each relation with relation index r from the set of all relations $\mathcal{R}$. In layer 2 204b, all of the entity nodes $202a_1$, $202b_1$, ..., $202h_1$ within the relation r from layer 1 204a that connect to entity node i $202a_2$ in layer 2 204b are represented by circles and the learned attention weights $\alpha_{r,i,j}$ shown as grey boxes, which are applied to each connection between each of the entity nodes $e_j \in \mathcal{N}_i^r$ $202a_1$, $202b_1$, ..., $202h_1$ in layer 1 204a and entity node $e_i$ $202a_2$ in layer 2 204b. For example, in layer 2 204b, the j-th entity node $202b_1$ $e_j \in \mathcal{N}_i^r$ $202b_1$, $\mathcal{N}_i^r$ being the set of all entity nodes that connect to entity node i within the relation r, connects to i-th entity node $e_i$ $202a_2$ with the learned attention weight $\alpha_{r,i,j}$ 206, which is applied to the connection 208 between entity node $e_j \in \mathcal{N}_i^r$ $202b_1$ and entity node $e_i$ $202a_2$. Each attention weight $\alpha_{r,i,j}$ is a single scalar that adjusts the amount of that input representation to add to the representation of the i-th entity node $e_i$ $202a_2$. For example, when $\alpha_{r,i,j}$ 206 is large, then i-th entity node $e_i$ $202a_2$ will use more of the input from the j-th entity node $e_1 202b_1$. When $\alpha_{r,i,j}$ 206 is small, then i-th entity node $e_i$ $202a_2$ will use less of the input from the j-th entity node $e_1$ $202b_1$. The GCNN technique 200 is configured to minimise the GCNN loss function based on the embeddings and the relationship scores and update the weights of the encoder network including the attention weights $\alpha_{r,i,j}$ for each edge of the graph and to update the weights of the scoring network (or decoder network). The attention weights $\alpha_{r,i,j}$ (a.k.a. scaling factors) of the graph are learned through training GNN model based on the GCNN technique 200 and data representative of the input entity-entity knowledge graph as the training graph dataset.

A model formation of the GCNN 200 is derived based on the model formulation of the conventional GCNN, which is based on computing a link prediction that includes two main steps: first, an encoding step (e.g. encoder network) for calculation of an embedding of entities of a entity-entity knowledge graph $\mathcal{G}$, and second, a decoding step (e.g. scoring network) to calculate the likelihood of a link or relationship between entities. Both steps, however, are linked as an end-to-end differentiable process.

The following is a model formulation for the conventional GCNN. A layer-wise GCNN formulation is based on:

$$H^{(l+1)} = \sigma\left(\tilde{D}^{\frac{1}{2}} \tilde{A} \tilde{D}^{\frac{1}{2}} H^{(l)} W^{(l)}\right)$$

where $\sigma(\bullet)$ is an element-wise activation function, which may be a nonlinear activation function such as, by way of example only but is not limited to, a ReLU function; an adjacency matrix $\tilde{A}=A+I_N$ with $A \in \mathbb{R}^{N \times N}$ of the undirected graph $\mathcal{G}$ with added self-connections from the identity matrix $I_N$; and the diagonal degree matrix $\tilde{D}_{ii}=\Sigma_j \tilde{A}_{ij}$ normalizing each node i. This formulation corresponds to a first-order approximation of localized spectral filters $W^{(l)}$ applied to an input signal $H^{(l)}$. This can be extended to multiple relations and the identity connection separated into a single self-relation. A simplification can be performed through subsuming the normalization matrix $$D^{\frac{1}{2}} \tilde{A} D^{\frac{1}{2}}$$

into a single pre-calculated constant matrix $C \in \mathbb{R}^{|\mathcal{R}| \times N \times N}$ for $|\mathcal{R}|$ relations and N nodes, resulting in the following conventional GCNN form for a single embedding $h_i$ for entity i for layer l+1:

$$h_i^{(l+1)} = \sigma\left(\sum_{r \in \mathcal{R}} \sum_{j \in \mathcal{N}_i^r} \frac{1}{c_{r,i,j}} W_{j,r}^{(l)} h_j^{(l)} + b_i^{(l)}\right)$$

where r is the relation index from the set of all relations $\mathcal{R}$, and j is the index of a node connecting to entity node i within $\mathcal{N}_i^r$, the set of all nodes that connect to node i within the relation r, the factor $$\frac{1}{c_{r,i,j}}$$

is a scale factor. Further, a node-specific layer-wise bias vector $b_i^{(l)}$ is applied to the embedding, with analogy to deep neural networks.

Three forms of the weight matrix $W_{j,r}$ may be considered in the order of the most parameters to the least number of parameters. In the first form or the unique representation of the weight matrix $W_{j,r}$, for the first hidden layer (with analogy to the success of embeddings in text applications) the fully general $W_{j,r} \in \mathbb{R}^k$ for a k-dimensional embedding is considered in which initially $h_j=1$ (a one-hot vector) providing a unique embedding for each entity and for each relation. Optionally in the second form or matrix representation of the weight matrix, the weight matrix may be shared across entities within a relation as a method to apply a common projection on a $k^{(l)}$-dimensional embedding to yield a $k^{(l+1)}$-dimensional one. That is, $W_{j,r}=W_r$, $\forall_j \in \mathcal{N}^r$ to yield a weight matrix $W_r \in \mathbb{R}^{k^{(l+1)} \times k^{(l)}}$. As another option in the third form or diagonal representation of the weight matrix, for further regularization, only the diagonal of the weight matrix can be occupied, yielding a kronecker product of the diagonal of $W_r$ and the input embedding $h_j$.

Furthermore, the embedding $h_i$ for entity i for layer l+1 can efficiently be computed as a series of matrix multiplications in which the following formulation may be used:

$$H^{(1)} = \sigma\left(B^{(0)} + \sum_{r \in \mathcal{R}} (C_r \odot A_r) W_r^0\right)$$

$$H^{(l+1)} = \sigma\left(B^{(l)} + \sum_{r \in \mathcal{R}} (C_r \odot A_r)(H^{(l)} W_r^{(l)})\right)$$

where $B \in \mathbb{R}^{|\mathcal{N}| \times k^{(l)}}$ dimensional bias for each embedding, $C_r \in \mathbb{R}^{|\mathcal{N}| \times |\mathcal{N}|}$ is a scaling factor for each connection between two nodes, the adjacency matrix $A \in \{0,1\}^{|\mathcal{N}| \times |\mathcal{N}|}$, the hidden representation $H^{(l)} \in \mathbb{R}^{|\mathcal{N}| \times k^{(l)}}$, and the weight matrix as above, optionally $W_r \in \mathbb{R}^{|\mathcal{N}| \times k^{(l)}}$, $\mathbb{R}^{k^{(l+1)} \times k^{(l)}}$ or effectively $\mathbb{R}^{k^{(l)}}$ respectively for the unique, matrix, and diagonal representations.

At the end of the encoding process (output of the encoding network), each entity is represented with an embedding vector e. As the choice of decoder (or scoring network) can be considered independently of the encoding system/network, a variety of methods from tensor factorization can be employed, including DistMult, TransE, ComplEx, Rescal, or others, as the choice can be made independently of embedding framework. For simplicity and by way of example only, the DistMult decoder is given by:

$$f(e_s, R_r, e_o) = e_s^T R_r e_o$$

which is comprised of the subject embedding $e_s$, the object embedding $e_o$, and the diagonal relation matrix $R_r$.

Training the network, which includes the encoding and decoding/scoring networks, consists of minimizing the cross-entropy loss on the link class $\in \{0,1\}$, enriched by negative samples created by corrupting either the subject or object of a relation with a random entity. Further, for stable training dropout was employed on the embeddings at each step of the computation, on the embedding relation projections, and on the links themselves unless otherwise specified. This can improve performance.

Further performance improvements may be achieved by including an attention weight in the embedding of the GNN model according to the invention as described with reference to FIGS. 1a-2a. The following describes an attentional model for interpretability of the connections within an undirected knowledge graph $\mathcal{G}$. Although others have examined the role of conventional attention mechanisms/models in graph networks, primarily to aid in transductive inference and to alleviate any issues caused by the inverse-degree normalization process used to calculate $C_r$, such attention models come with a considerable computational cost and have to learn to predict which features of a left and right entity would inspire a strong link or condemn a weak link.

Rather, the attention mechanism used by the present invention and disclosed herein uses a more general form, in which each link (e.g. connection/relationship edge between entity nodes) has an independent, learnable attention weight that is a function of the truthfulness or relevancy of that link/connection (e.g. relationship edge). A link's weight might be independent of the features at each entity node, and instead should be learned according to global consistency through the aggregate training (e.g. through the loss function of the GCNN technique). Incorrect links (connections) of the knowledge graph $\mathcal{G}$ will be diminished as noise, inconsistent with the other relationships of the entity node, and the attention model according to the invention can learn to suppress the links/connections corresponding to incorrect facts.

The embedding of the conventional GCNN is modified to include an attention weight for each relationship edge (e.g. link/connection) of the knowledge graph, the embedding $h_i^{(l+1)}$ for the modified GCNN for training the GNN model for entity node i and layer l+1, for $0 \leq l$ is an N-dimensional vector $h_i^{(l+1)}$ defined by:

$$h_i^{(l+1)} = \sigma\left(\sum_{r \in \mathcal{R}} \sum_{j \in \mathcal{N}_i^r} \alpha_{r,i,j} W_{j,r}^{(l)} h_j^{(l)} + b_i^{(l)}\right)$$

where r is a relation index of a relationship from the set of all relationships $\mathcal{R}$ associated with the relationship edges of the entity-entity graph, and j is the index of an entity node connecting to entity node i within $\mathcal{N}_i^r$, $\mathcal{N}_i^r$ the set of all nodes that connect to entity node i for relation index r, $\alpha_{r,i,j}$ is the attention weight associated with the connection between entity node i and entity node j for relation index r, $b_i^{(l)}$ is a node-specific layer-wise bias vector applied to the embedding $h_i^{(l+1)}$, $W_{j,r}^{(l)}$ is the associated relationship adjacency matrix for the l-th hidden layer associated with entity node i, and σ(•) is an activation function.

The GCNN loss function, $\mathcal{L}$ (•), may be minimised by: assigning an attention weight, $\alpha_{r,i,j}$, to each link/connection (e.g. relationship edge) of the entity-entity knowledge graph, where $\alpha_{r,i,j}$ is the attention weight associated with the connection/link between entity node i and entity node j with relation index r of the plurality of relationships in the set of all relationships $\mathcal{R}$ associated with the knowledge graph; modifying the GCNN loss function, $\mathcal{L}$ (•), by adding an attention loss function or cost function, $\mathcal{L}_{att}(\hat{\Lambda})$, associated with the set of attention weights $\hat{\Lambda}=\{\alpha_{r,i,j}\}$ to the GCNN loss function, $\mathcal{L}$ (•), where the modified loss function is $\mathcal{L}_{mod}$ (•)=$\mathcal{L}$ (•)+$\mathcal{L}_{att}(\hat{\Lambda})$; and minimising the modified loss function, $\mathcal{L}_{mod}$, with respect to the weights of the GNN model including the attention weights.

To further minimise the influence of stochastic initialisation, all embeddings may be initialised to an $l^2$-norm of 1, so that they all contribute equal magnitude to the embedded representation. Further, to provoke a contractive cost on the use of edges, an $l^1$-norm is added to the GCNN loss function (or cost function) $\mathcal{L}$ (•) by including an attention cost/loss function $\mathcal{L}_{att} = \lambda \Sigma_{\mathcal{R}} \Sigma_i \Sigma_{j \in \mathcal{N}_i} |\alpha_{r,i,j}|$ where λ is a hyperparameter, which may be a selected to be a suitably small cost weighting factor.

Additionally, constraining the total attentional budget can be beneficial. Thus, normalizing the sum of the attention weights such that there is a constant amount of input adds an additional constraint to encourage the attention model/mechanism to select useful links that maximally aid in predicting true facts. Each of the updated attention weights $\alpha_{r,i,j}$, is regularised to a normalised attention weight $\alpha'_{r,i,j}$. That is, the attentional connection weight after scaling may be defined as:

$$\alpha'_{r,i,j} = \frac{1}{\Sigma_r \Sigma_j |\alpha_{r,i,j}|} |\alpha_{r,i,j}|$$

where the attention weight $\alpha_{r,i,j}$ is initialized to 1 at the start of training, yielding the standard formulation that $\alpha'_{r,i,j}=1/|\mathcal{N}_i|$ for all j at the start of training the GNN model.

All of the operations for calculating the attention weights can be implemented with sparse tensor operations, with particular use of sparse_tensor_dense_matmul to perform a sparse multiplication of the adjacency matrix by the projected embeddings, and scatter_nd to sum the attentional connection weights across rows. This produces an efficient implementation proportional in cost to the number of edges, and particularly tuned to batch processing, as all embeddings can be generated simultaneously.

The GNN with attention weights according to the present invention may provide an augmentation with textual features. Unstructured textual data is a complementary information source to structured knowledge graphs. Text can contribute edges missing from the knowledge graph, whilst the domain of a KG (the space of possible triples) represents almost infinite numbers of facts never observed in text. The attention mechanism according to the invention allows, by way of example only but is not limited to, a GCNN based GNN model to exploit these separate sources of information in a natural way, simply by augmenting the graph with relationship edges (e.g. links) extracted from text, $\varepsilon = \varepsilon_{KG} \cup \varepsilon_{text}$. This gives a total set of attention weights:

$$\hat{\Lambda} = \bigcup_{r \in \mathcal{R}_{KB} \cup \mathcal{R}_{text}} \Lambda_r$$

where $\Lambda_r = \{\alpha_{r,i,j}\}$ is the set of attention weights for edges of relationship type r, in which r can be a relationship from the knowledge graph or a relationship extracted from text.

Textual links extracted via unsupervised methods contain proportionally more noise than curated structured facts. The GNN model is able to make use of the extra connectivity induced, without being mislead by these incorrect facts since it learns each $\Lambda_r$ independently. It can place weight only on those text edges which connect truly similar entities, whilst ignoring those arising from noisy extraction.

Previously, others have investigated methods for establishing feature importance in large, complex models such as deep networks. Gradient-based methods have arrived at the forefront because the calculation of all combinations of feature occlusions is prohibitive in cost, and these methods tend to offer an advantage. However, as a first-order approximation occlusion can be simply leveraged within the modified GCNN framework according to the invention; simply setting the link weight to zero and measuring the change in prediction likelihood allows an estimate to be made regarding the relative importance of that link for the given prediction. As the implementation here and elsewhere focuses primarily on shallower implementations leveraging flexible embeddings equipped with relatively simple linear combinations, this is perhaps more predictive than in the highly nonlinear space of deep CNNs. Further, this can be extended to the nodes themselves: a large attention weight would suggest that that link has a larger influence on the output of predictions in general.

The performance of the modified GCNN technique that generates a graph model (or attentional GCNN model) based on a synthetic entity-entity graph, a graph derived from public knowledge bases, and a graph derived from large proprietary dataset, which include a mix of noisy and clean relational data; in the context of the latter dataset, a demonstration of how one might achieve a first-order approximation of model interpretability follows.

A series of experiments are performed using synthetically generated graphs. There are two motivating factors behind this. First, the use of these graphs allows the performance of the graph model according to the invention to be validated in a controlled setting. In particular, both a clear delineation between true and false edges can be specified, and also a level of graph incompleteness; in almost all real knowledge graphs and other networks, the former is, itself, noisy, while the latter is unknown (but, given the need for link prediction, most certainly non-zero). Second, because there are classes of graph evolution models that aim to mimic the evolution of real-world networks, experiments on these generated networks allow the demonstration of a set of downstream applications in network evolution parameter inference and model selection downstream of the original link prediction task. The experiments are based on the Duplication-Divergence (DD) model, which is undirected graph with single edge-types and a biologically-inspired generative model of protein-protein interaction networks.

The DD Model is a four-parameter model (π,p,q,r) that models the growth and evolution of protein-protein interaction networks. The biological and evolutionary rationale for this example is simple: organisms evolve from simple to complex forms through favourable random mutations of existing (protein-encoding) genes and the creation of new ones; a genetic mutation is far less likely to be deleterious when there are multiple copies of the gene, which are crated most probably by gene duplication events.

Given a (small) starting seed graph $G_0$ with genes as nodes and edges representing the interaction between their encoded proteins, the model aims to mimic this evolutionary process as follows. First choose a node $n_{old}$ in $G_0$ uniformly and create a new node $n_{new}$. Next, apply one of the following two rules:
1. Create an edge between $n_{new}$ and $n_{old}$ with probability q and create edges between $n_{new}$ and any other node linked to node $n_{old}$, each with probability p.
2. Create an edge between $n_{new}$ and $n_{old}$ with probability r.

In every step rule 1 is followed with probability $\pi$ and rule 2 is followed with probability $1-\pi$.

In the experiments for the DD Model, $G_0$ is a 2-node graph connected by a single edge. The following parameters are fixed to $\pi=1$, $q=0.5$ and $p=0.8$ and the graphs are grown to a final sizes of 100 and 1000 nodes. The values of p and q are chosen to ensure that the sub-sampled graph has a single connected component. It is noted that the parameter r is redundant when $\pi=1$, which is the case here. This corresponds to the not entirely unrealistic scenario of a zero-probability of a random appearance of a gene.

There are three objectives for the following set of link prediction experiments on the DD model network:
1. To show an improvement in performance by incorporating the attention mechanism into the GCNN framework;
2. To demonstrate a robustness to false edges, noise, in the graph as compared to GCNNs without learned attention edge weights, and other link prediction algorithms.
3. Provide a basic form of interpretability via the unsupervised learning of link weights.

For each graph the edges are randomly divided into three equally-sized subsets which are referred to as train-gold, train-add, and test, with the natural condition that all the nodes of the original graph are represented in train-gold (this is to allow one to learn the representation of every node). Several different training sets are created by combining train-gold, train-add, and different sets of randomly generated false edges, which are referred to as train-noise. As a proportion of train-add, noise levels from the set {0.0,0.25, 0.5,0.75,1.0} are considered. A training set is also built comprising only of train-gold. The test dataset is reserved for evaluation.

The above setup recreates the situation where one has an incomplete, but high-precision, dataset (train-gold) with which to train a GNN model for link-prediction, together with the option of supplementing the graph model training with a set of additional, but possibly noisy, relations (train-add ∪ train-noise). In the context of GCNN techniques, this fully augmented set is used to define the training graph adjacency matrices for use in learning the node and relation embeddings, where in $$h_i^{(l+1)} = \sigma\left(\sum_{r \in R} \sum_{j \in N_i^r} \frac{1}{c_{r,i,j}} W_{j,r}^{(l)} h_j^{(l)} + b_i^{(l)}\right).$$

$N_i^r$ is defined from all the edges in (train-gold ∪ train-add ∪ train-noise). However one can choose to train only on the relation triples in train-gold or on the full noisy set. Both approaches are compared in the experiments. The full set of hyperparameters for the graph model is provided below.

Figure 3A:
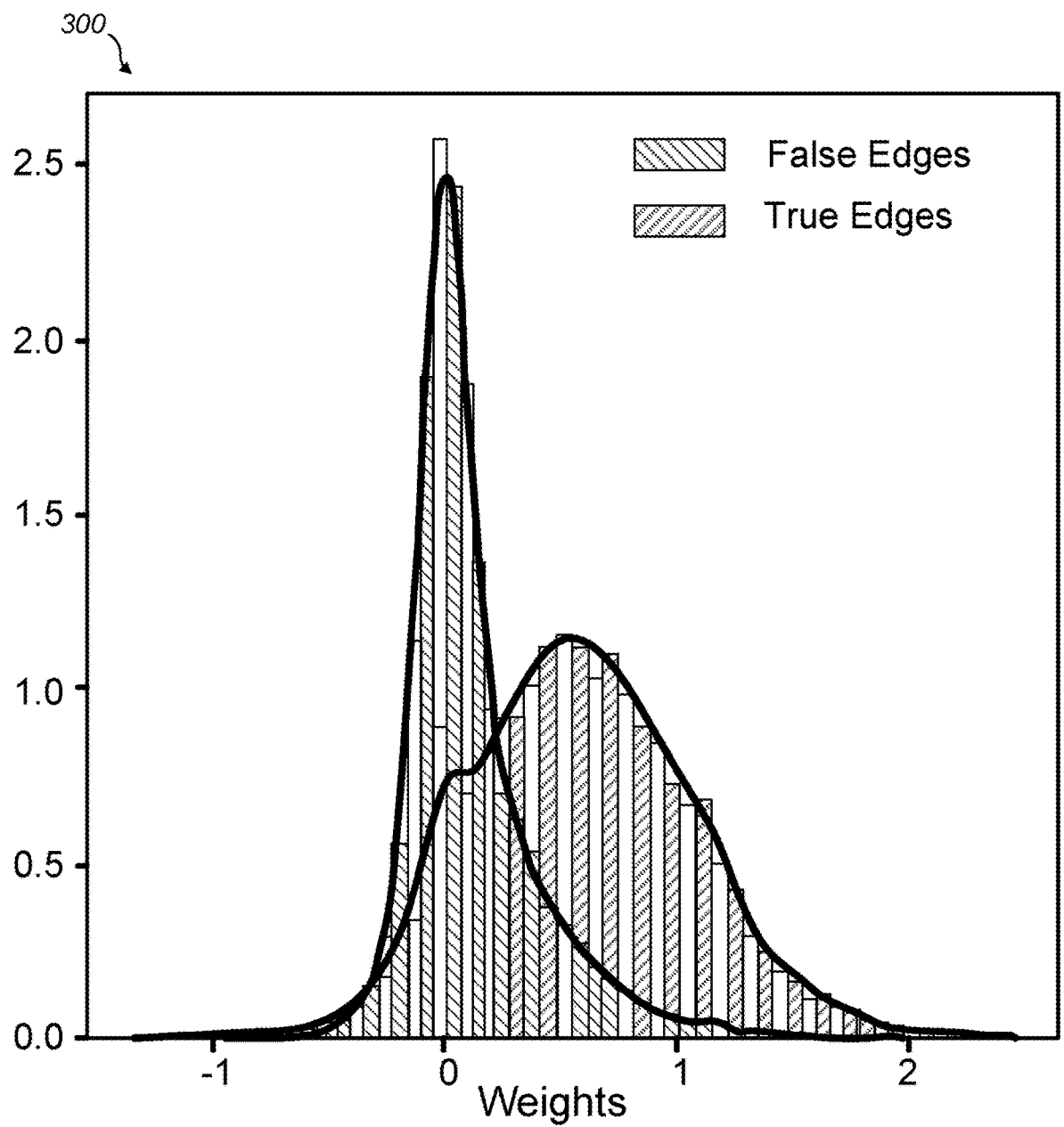
FIG. 3a is a diagram illustrating the distribution of true weights and false weights of the GNN model based on FIG. 2 according to the invention.
Figure 3B:
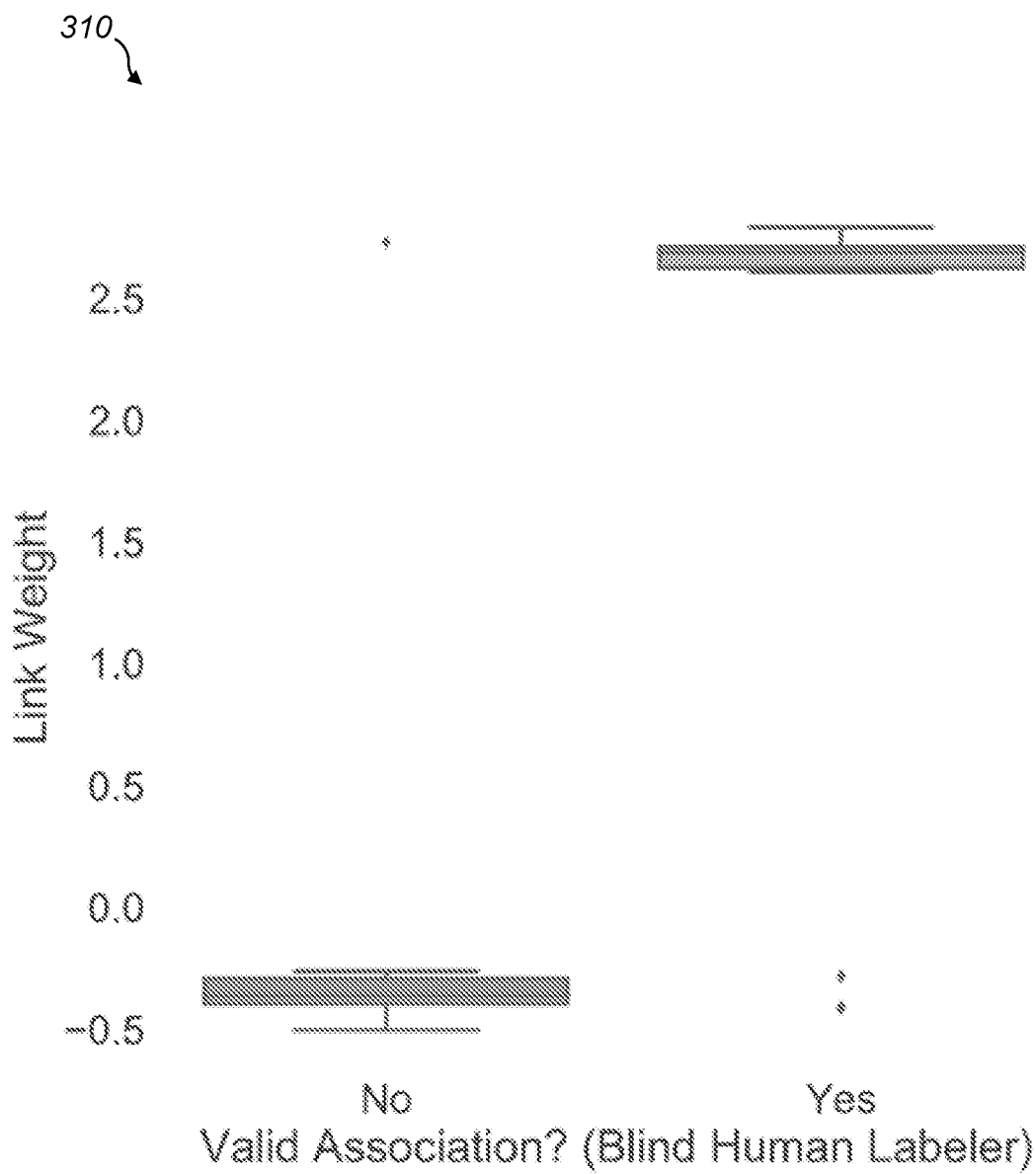
FIG. 3b is a graph illustrating the link weight vs valid association of a GNN model based on FIG. 2 according to the invention.

The results of the experiments are presented in the following figures. FIG. 3a illustrates a graph 300 of the distribution of true weights and false weights on a synthetic dataset. Note that the training process of the modified GCNN technique to generate the graph model successfully separates true weights from noise weights representing false edges. FIG. 3b is a graph 310 illustrating the link weight vs valid association of a GNN model according to the invention. The graph 310 of FIG. 3b is the result of blind human labelling of high and low weight edges in a model trained on a real-world biological knowledge graph augmented with a set of relationships extracted from the scientific literature. As can be seen, the GNN model accurately predicts the majority of the high and low weight edges; a couple of outliers are shown as false positive and false negatives.

As shown, the modified GCNN technique with attention weights according to the invention for generating graph models outperforms the complex conventional attention models. The modified GCNN technique with attention outperforms GCNN without attention. The modified GCNN technique with attention is robust to noise. The modified GCNN trained on all datasets outperforms conservative estimates.

The ability of the modified GCNN technique to identify false links has wide implications for graph model interpretability and a host of downstream tasks. The area of network model inference is demonstrated.

Table 1 demonstrates the results on the public FB15k-237 dataset. As seen in the synthetic dataset experiments, four conditions were trained. To establish a baseline, the full dataset is trained in the normal methodology ("clean"), and the results here compare favourably to previous studies. Next, the training data is randomly split in half, and the results reported are the performance on the test set when training solely on half of the training data ("50%"). Next, the "Gold" condition refers to training solely on half of the training data, but adding the remaining 50% of the training data to the adjacency matrix alone, mixed 1:1 with noise. In effect, this results in ⅓rd of the edges in the adjacency matrix arising from noise, to model the condition of adding facts to the KG with varying noise levels. Finally, the "Noised" condition includes training on those noisy edges that are present in the adjacency matrix, whereas the edges are only present (and not trained upon) in the adjacency matrix in the "Gold" condition.

The results in Table 1 demonstrate that the GCNN model does indeed outperform the standard tensor factorisation techniques. Furthermore, the GCNNs with attention outperform GCNNs without, particularly in the low-data domain or when significant noise is added. In the low-data domain, the attention factor may help renormalise inputs more effectively than a raw calculated weight; when significant noise is added, the weighting factor can allow the network to downgrade the importance of particular edges. In either case, it appears to be an effective aid. Note that standard tensor factorization techniques cannot allow for a difference between the data used to form the representation of the entity and the data used to predict the existence of an edge, whereas GCNNs permit a distinction. Uniquely, as the data used to form the adjacency matrix does not need to match the training data, GCNNs can indeed treat training data differently from representation data, corresponding to the "Gold" condition in Table. 1, in which only 50% of data is trained on while 100% of the training data (plus noise) forms the adjacency matrix. Note that in this case, the GCNN with attention impressively nearly recovers the performance of using a pure, clean training set of 100% of the data while training on only half.

Again, the GCNN-attention model demonstrates:
- modified GCNN technique outperforms complex attention systems;
- GCNNs with attention outperform GCNN without
- GCNNs with attention are robust to noise
- GCNNs trained on all outperforms conservative estimate, the latter performs particularly poorly, however
- The weight separation is greatest for training only on the golden set—give a rationale along the lines of the model not obliged to predict false edges.

TABLE 1

Performance on FB15k-237 Datasets

| Algorithm | Hits@1 | | | | MRR | | | |
|---|---|---|---|---|---|---|---|---|
| | Clean | 50% | Gold | Noised | Clean | 50% | Gold | Noised |
| DistMult | 12.8 | 9.6 | — | 14.8 | 21.7 | 17.3 | — | 22.7 |
| ComplEx | 13.9 | 9.8 | — | 12.9 | 22.1 | 17.3 | — | 21.0 |
| GCNN | 15.8 | 11.9 | 7.4 | 13.8 | 24.8 | 20.9 | 18.7 | 22.7 |
| Modified GCNN w/att | 15.9 | 13.7 | 15.5 | 15.5 | 25.4 | 22.4 | 24.4 | 24.2 |

TABLE 2

SLP dependency path relation

| | |
|---|---|
| Subject: | 'nsubj', 'nsubjpass', 'xsubj' |
| Object: | 'dobj' |
| Clausal Modifier: | 'acl', 'acl:relcl' |

TABLE 3

Performance on the FB15k-237 Dataset augmented with SLP relations

| Model | MRR | H@10 | H@3 | H@1 |
|---|---|---|---|---|
| DistMult | 0.270 | 0.4479 | 0.299 | 0.182 |
| ComplEx | 0.282 | 0.467 | 0.312 | 0.191 |
| GCNN/DistMult | 0.283 | 0.485 | 0.312 | 0.185 |
| GCNN/Complex | — | — | — | — |
| Modified GCNN w/att DistMult | 0.292 | 0.497 | 0.321 | 0.195 |
| Modified GCNN w/att ComplEx | — | — | — | — |

Textual Augmentation is performed on the FB15k-237 dataset to include SLP relations. Experiments to augment the KG were performed with textual data, using the text dataset that consists of 2.7 million unique relations extracted from the ClueWeb12 corpus. Textual relations are defined as the directed, lexicalized dependency between two entities which co-occur in a given sentence. This number of sparse mentions is due to the variety of largely synonymous surface forms which may describe any one relation type. The number of distinct relationships is reduced by defining syntactically linked pairs (SLPs). An SLP is a 2-tuple of entities which occur within a sentence where the two entities are linked via a meaningful grammatical construction. This is determined by inspecting the dependency path for the inclusion of a number of different dependency relations, as shown in Table 2. For a subject relation, if one of the arguments is a verb, it is chosen as the predicate; otherwise it is a copula verb, and the other argument is chosen as the predicate. The relationship type between these entities is defined as an ordered pair (verb, relation), which is referred to as an SLP-relation.

The free open-source library spaCy for Natural Language Processing is used to perform part-of-speech tagging on the terms in these dependency paths, as required by the SLP algorithm. After filtering, 63,406 unique SLP-relation types are obtained. For computational tractability only the top N most frequent relations. For $N \in \{3, 10, 20\}$ this gives $\{69045, 139341, 185535\}$ extra edges which can be added into the graph (compared with 272, 115 structured edges in the FB15k-237 train set). This gives a composite graph with $\{276, 283, 293\}$ separate relation types respectively. The test and validation sets remain unchanged. In line with the synthetic dataset experiments, the proportion p of total available SLP edges that can be used to augment the graph is treated as a hyper-parameter with optimisation over $p \in \{10\%, 20\%, 50\%, 100\%\}$. Results are obtained for both a single and two-layer GCNN. In all cases the single layer model was found to perform marginally better and train $\approx 2\times$ faster. As well, using SLP relations only as new edges in the adjacency matrix (c.f. Gold, above) and including them as part of the training data was investigated. This is analogous to a multi-task learning setting in which the auxiliary task of fitting text relations is useful for the main task of predicting KG relations. Training directly on SLP relations was found to yield better performance. Hyperparameters were optimized based on mean reciprocal rank (MRR) performance on the validation set. Results for training directly on SLPs, with N=20 and p=20% are displayed in Table 3.

As an example use case on production data, a subset of an in-house knowledge graph with 708 k edges is considered, which comes from unstructured data sources including National Centre for Biotechnology Information (NCBI) PubMed full article text and a variety of structured sources including the Comparative Toxicogenomics Database (CTD), Kyoto Encyclopedia of Genes and Genomes (KEGG) database, Online Mendelian Inheritance in Man (OMIM) database, the biogrid interaction database (BioGRID), Omnipath, and The chembl bioactivity database (ChEMBL) among others. Selecting a very small subset of 27 k edges of the data as gold-standard data chosen from manual curation, and using the remaining training data only within the adjacency matrix, permits performing the interpretability experiments first investigated above in the synthetic data.

Figure 3C:
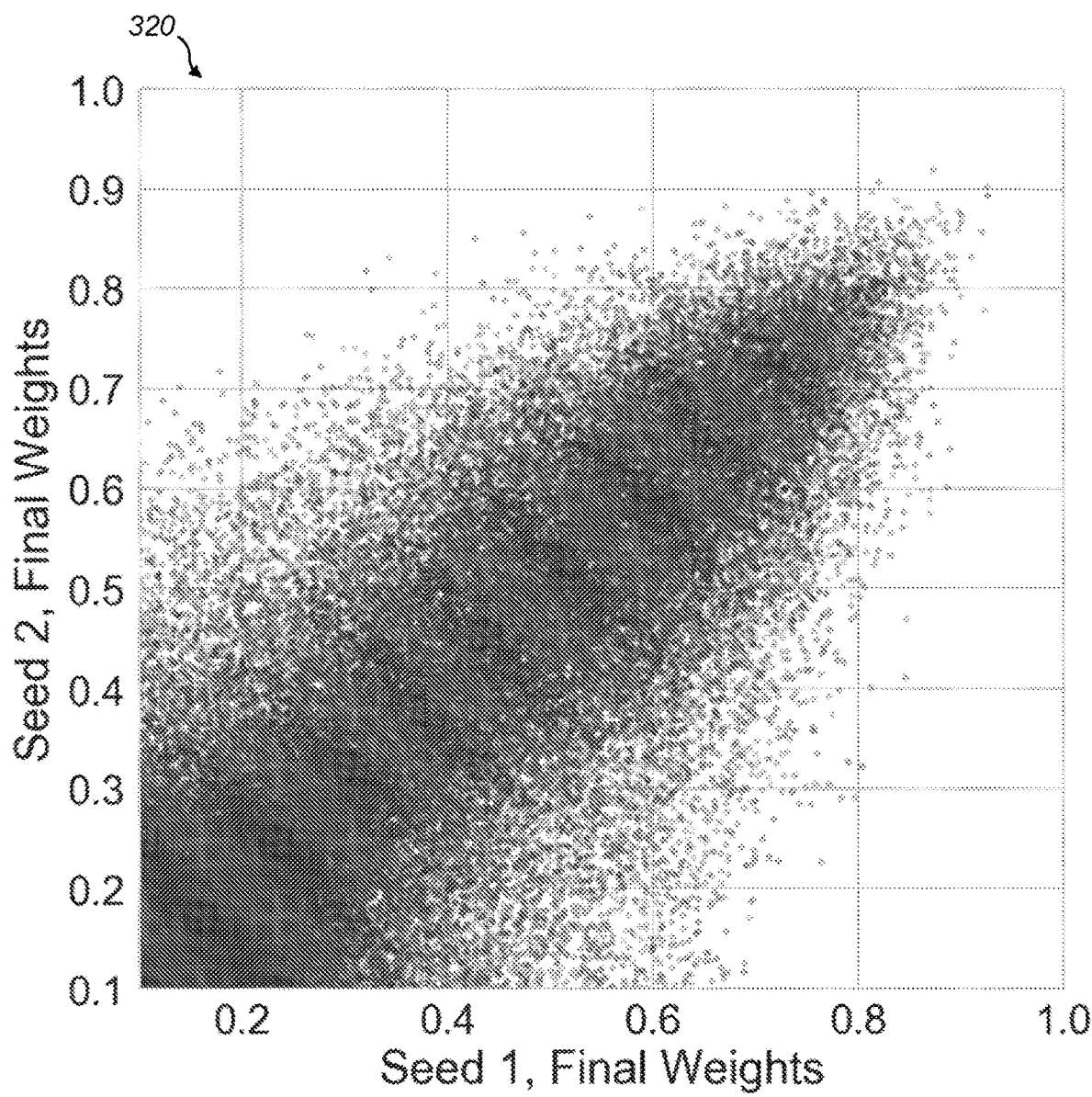
FIG. 3c is a graph illustrating self-similarity of weight edges of a GNN model based on FIG. 2 according to the invention.

Initially, the weights are examined to ensure that they have an inherent consistency despite random initial conditions. FIG. 3c is an illustration of a graph 320 illustrating self-similarity of weight edges of the resulting graph model according to the invention. Self-similarity of weight edges from two random initializations on the production real-world dataset. Note that despite different initial conditions, most attentional connection weights end training at similar magnitudes and thus lie along the diagonal. FIG. 3c plots the weights of relations extracted from unstructured text between genetic targets and diseases, and shows remarkable consistency across training runs. If the weights had no interpretable meaning, then subsequent runs would generate a cloud of points with no discernible correlation structure. Instead, a given extracted edge typically falls into a similar weight value despite random initial conditions, creating the diagonalized visible structure and a strong Pearson's correlation coefficient of r=0.882. It is worth noting that higher-weighted links appear to have higher consistency than low-weighted ones.

Figure 3D:
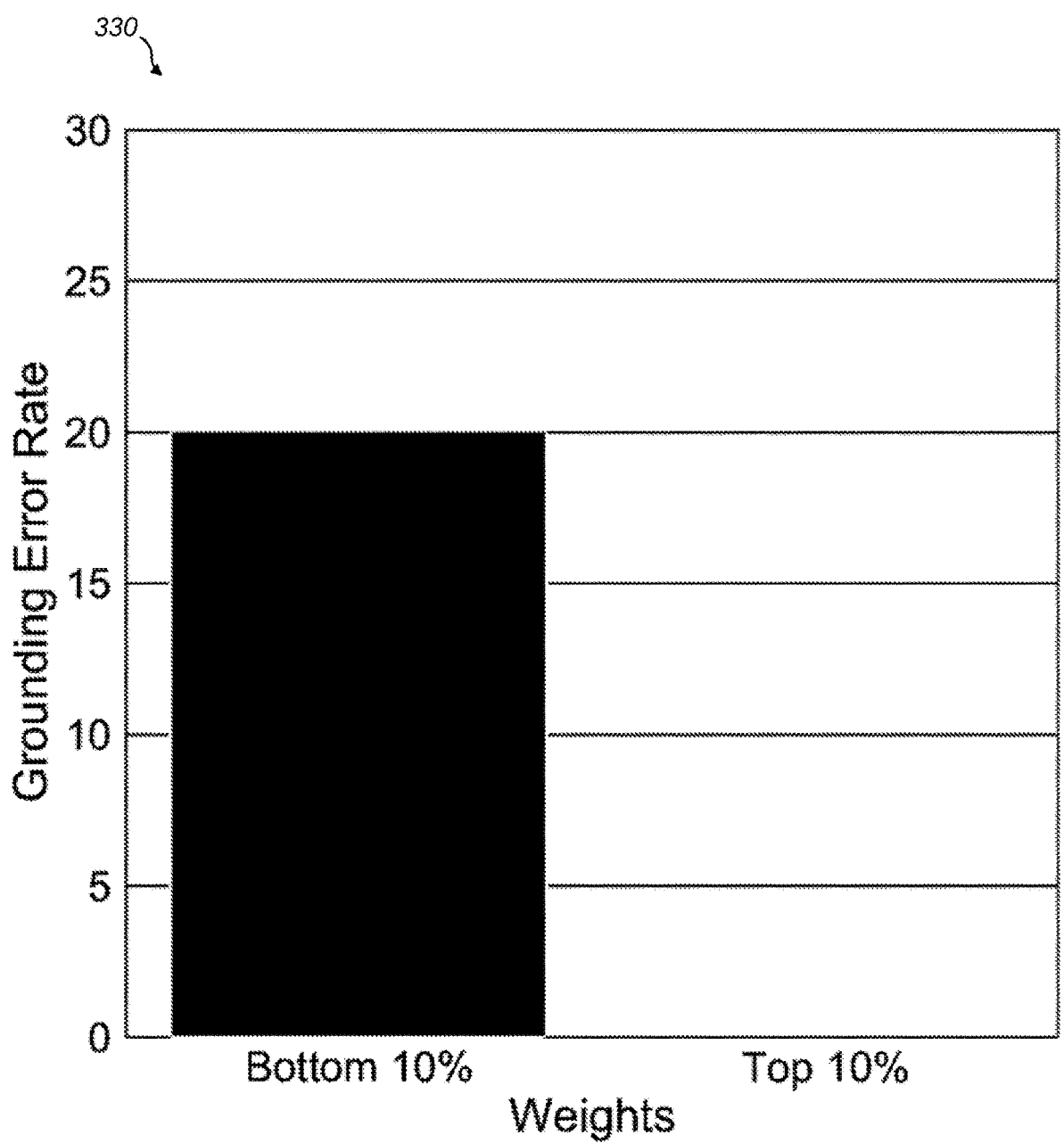
FIG. 3d is a graph illustrating weights vs grounding error rate of a GNN model based on FIG. 2 according to the invention.

Next, the hypothesis that low weights imply decreased usefulness is examined. In its most primitive form, this can be tested by blind evaluation of extracted edges from unstructured data sources. As data extraction is known to be a challenging task, particularly in biomedical literature, there are expected to be edges extracted which do not pass a manual evaluation. For example, abbreviation collisions can be common. After extracting a number of edges, and blindly evaluating whether the text implies a relation between the suggested disease and target, a first number of errors appeared in edges sampled from the bottom 10% of weights, and a second number of errors appeared in edges sampled from the top 10% of weights, as seen in FIG. 3d. FIG. 3d illustrates a graph 330 of weights vs grounding error rate, where a grounding error is said to occur when one of the two entities is incorrectly identified. This can occur, for example, when two entities have the same abbreviation or synonym.

Figure 3E:
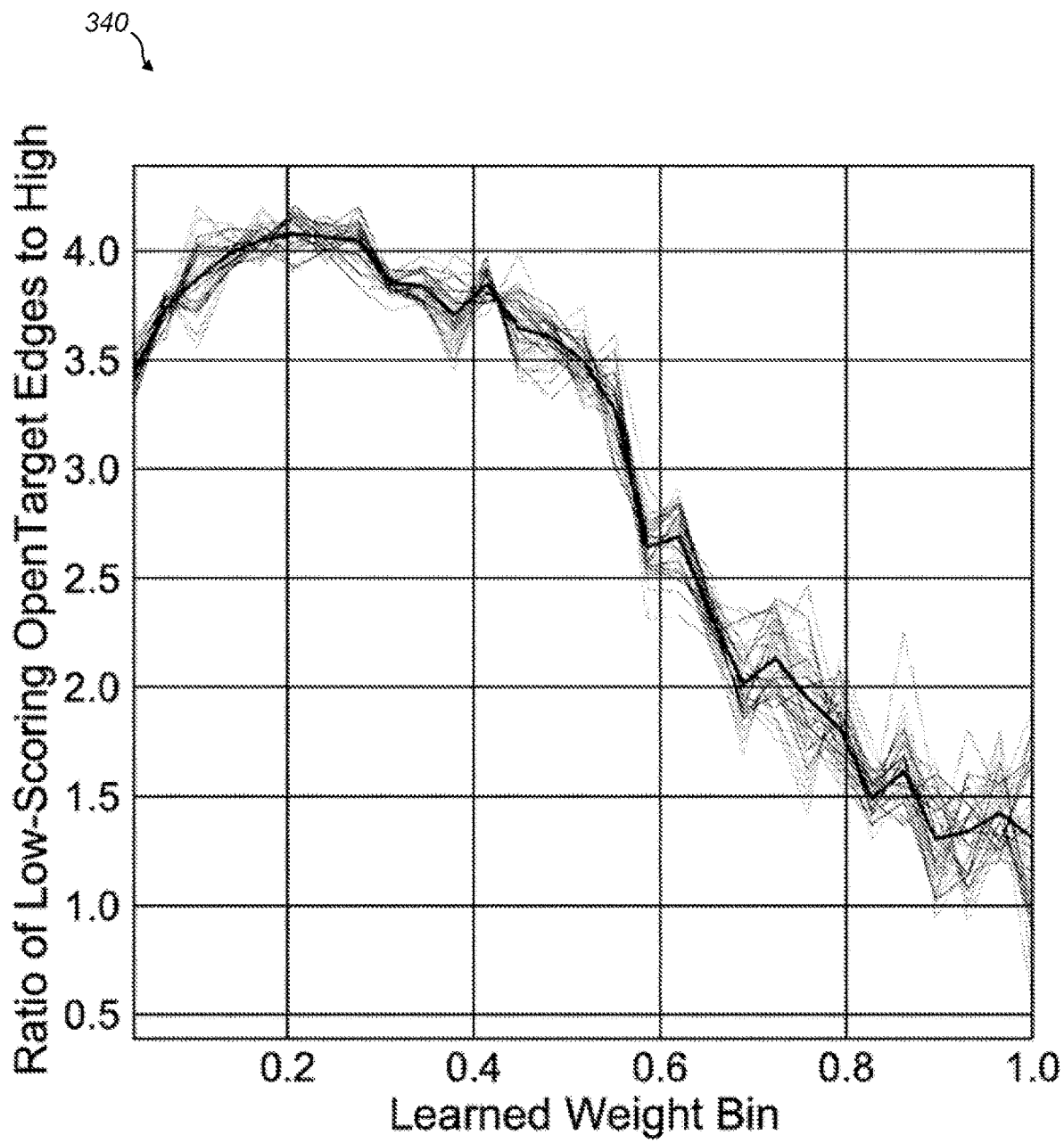
FIG. 3e is a graph illustrating of learned weight bin vs the ratio of low-scoring OpenTarget edges to high of a GNN model based on FIG. 2 according to the invention.

Next, there is another level of incorrectness that can occur: it is possible for the text extraction to occur perfectly, but for the scientific evidence of a relationship between a disease and a target to be weak or even spurious. To estimate this type of error, edge weights can be compared with their corresponding scores, if they exist, in the Open Targets platform, which is a platform for therapeutic target identification and validation. The Open Targets project weighs scientific data from multiple sources to produce a score between diseases and targets, providing an estimate of the confidence in these relationships. Surprisingly, the GCNN attention weight can even predict this quantity; FIG. 3e illustrates a graph 340 of learned weight bin vs the ratio of low-scoring OpenTarget edges to high and demonstrates the results. In this test, five different random seeds were used, and training was performed using the gold-standard training technique outlined above. After training, the weights corresponding to edges extracted from unstructured text connecting diseases and targets were separated into two groups. The first group corresponds to edges that exist in the Open Targets platform, but have a score below 0.1, indicating low confidence. The second group corresponds to edges that have an Open Targets score above 0.9, indicating a high confidence. After organizing the weights in histograms of 30 bins, the likelihood of a weight at a given magnitude belonging to a low or high Open Targets score was empirically estimated. As FIG. 3e illustrates, a low-weighted edge is 4 times more likely to be a low-scoring Open Targets edge than a high-weighted one. At higher weights, this ratio drops to nearly parity, making high-scoring Open Targets edges much more likely. A 2-sample Kolmogorv-Smirnov test yields p=6e−28, strongly rejecting the hypothesis that these two weight distributions arise from the same underlying distribution and suggesting that the weights have an interpretable meaning related to their correctness.

Figure 4A:
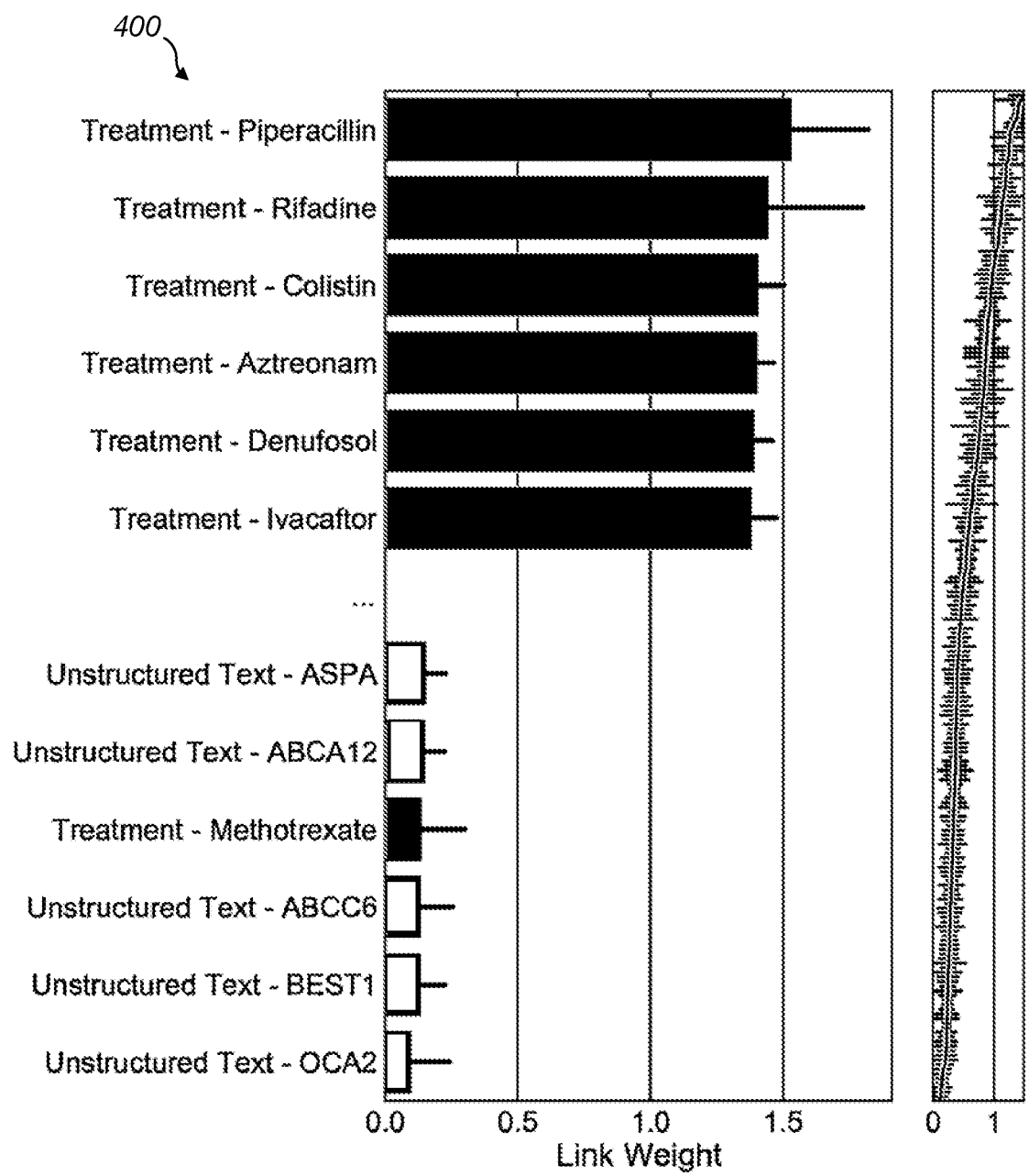
FIG. 4a is a graph illustrating the ranking of an entity node's influencers of a filtered graph from a GNN model based on FIG. 2 according to the invention.

In addition to their advantage for noise robustness, GCNN provide greater interpretability compared to alternative models such as tensor factor models. As an entity's representation is calculated in a separate step from the link prediction, there are new opportunities to visualize an entity in terms of its connections. By sorting by mean weight across models and including the standard error of the score, it is possible to visualize the most and least important factors for a representation. For example, FIG. 4a illustrates a graph 400 illustrating ranking of a node's influencers and shows a visualisation for the disease "Cystic Fibrosis". It is possible to view that the strongest influences on the entity's representations are formed by a class of drugs that are listed as treatment for cystic fibrosis in curated databases. Two of the top six connections (e.g. the top-most six black bars) are drugs specific for Cystic Fibrosis management (e.g. Denufosol and Ivacaftor), while the other four are antibiotic drugs that are often used to manage infections arising in Cystic Fibrosis. In the other hand, the six lowest-weighted links (e.g. the lower-most six small bars, 5 white bars and one black bar with link weights less than approximately 0.25) consist of targets and a treatment that are either spurious or more remotely related to cystic fibrosis. Connections with ABCC6 and ABCA12 arise from false relation extraction; cystic fibrosis and these genes are merely mentioned in the same sentence as part of a list but with no functional connection. Connections with the other three targets are also false or weak: for example, while OCA2 is differentially expressed in Cystic Fibrosis, its function in melanin production is not aligned with the disease pathophysiology. Such investigations of high- and low-weighted connections illustrate how visualizations can empower researchers and users to address fundamental issues of noise in knowledge graphs; based on these learned connection strengths, users can provide feedback and edit edges to improve knowledge graph quality based on the attention weights learned by the GNN model.

Figure 4B:
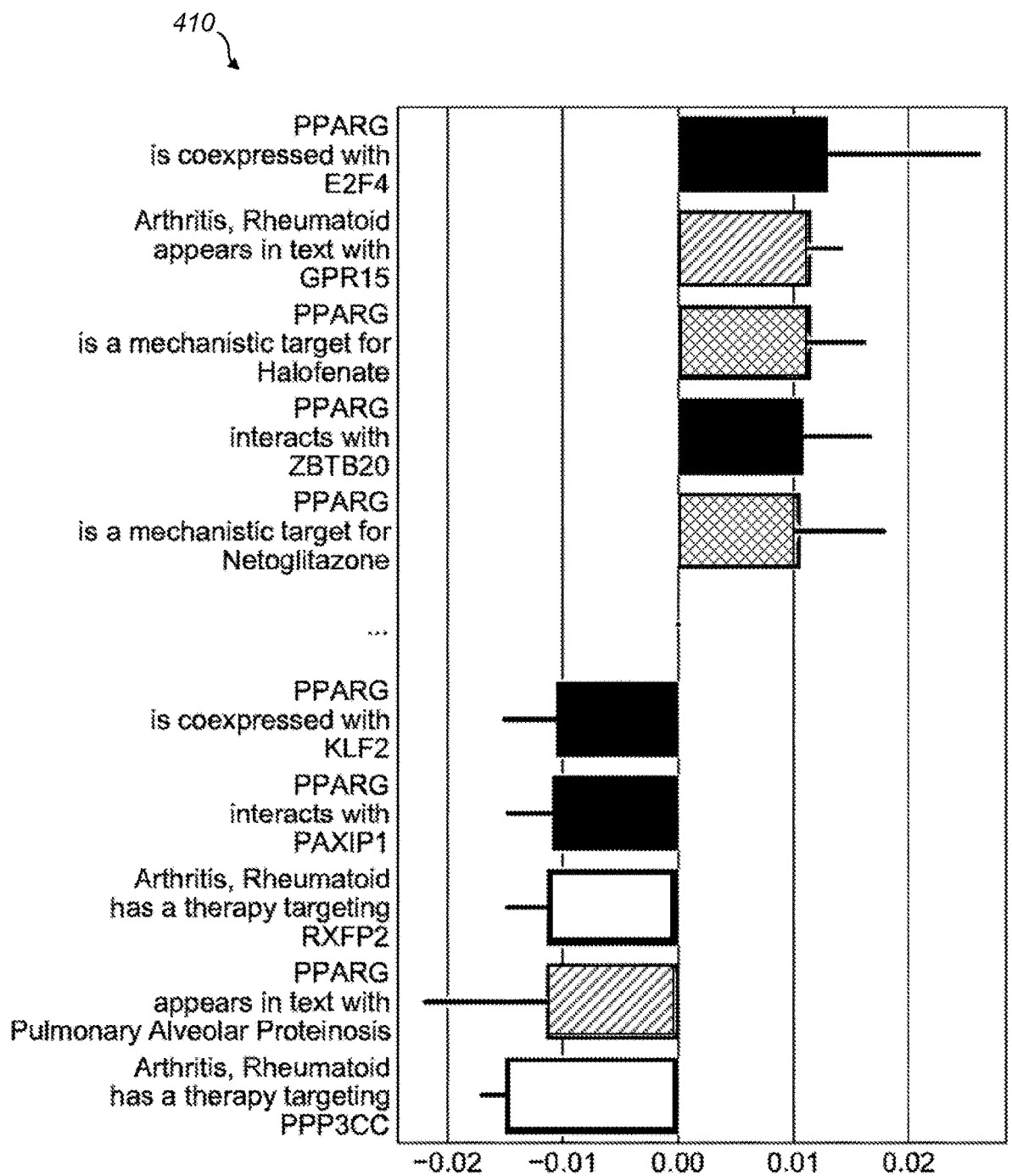
FIG. 4b is a graph illustrating prediction score vs drug target of a filtered graph from a GNN model based on FIG. 2 according to the invention.
Figure 4C:
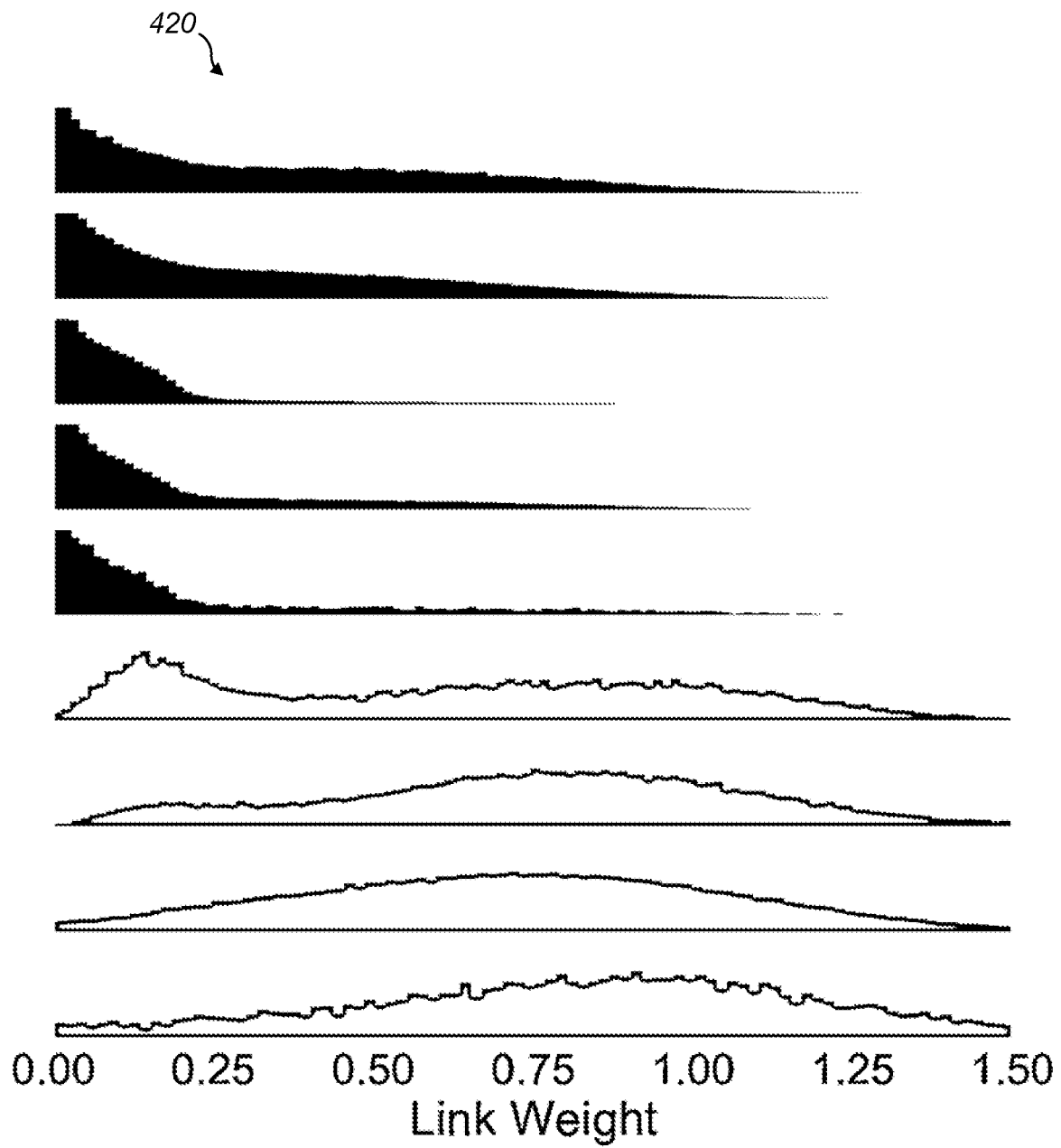
FIG. 4c is a graph illustrating overall confidence trends in the learned weights for each relation type of an entity-entity graph for a GNN model based on FIG. 2 according to the invention.

One of the major advantages of GCNNs is that an edge can be added or removed after training. This bears similarity to the feature occlusion methods used for interpretability in high-dimensional CNNs. As these networks are trained with dropout and can be robust to the loss of an edge during prediction, it is possible with the GNN model based on GCNNs according to the invention to selectively remove an edge during prediction alone to measure its effect on the relationship score or prediction score. This process can be seen in FIG. 4b. FIG. 4b illustrates a graph 410 of prediction score (e.g. relationship score) vs drug target for evaluating the possibility of PPARG being a drug target for Rheumatoid Arthritis. Each bar demonstrates the effect that fact has on prediction score. All inputs to both the left and right of a relation are independently removed. Here, the prediction is to determine if PPARG can be a therapeutic target for the disease Rheumatoid Arthritis, which is a true edge that has been hidden during training. The top positive driver is that the target in question is coexpressed with E2F4, a target implicated in rheumatology. Furthermore, the strongest negative driver is that Rheumatoid Arthritis has an existing therapy targeting PPP3CC, which is a gene target more widely implicated in schizophrenia, a quite different disease. Moreover, interrogating the GNN model according to the invention builds confidence in the GNN model's predictions Finally, beyond inspecting weights at the link level, data sources as a whole can be examined. FIG. 4c illustrates a graph 420 that shows overall confidence trends in the learned weights for each relation type. The edge histograms that are coloured solid white with a black border corresponds to edge types that were trained upon, while the solid black histograms correspond to edges present only in the adjacency matrix; as expected, the latter edges (e.g. solid black histograms) are typically downweighted in favor of edges trained upon. Additional patterns, however, are also quite visible. For example, the top two edge types contain proportionally more high-weighted edges than those below, and in fact the third from the top has strongly shifted its distribution toward around zero, implying that the model does not find most of the relation useful. Even within edge types that are trained upon, there appears to be a bimodal distribution, suggesting a noisy data source with both highly predictive edges and distracting edges. Using this information, cleanup or removal of entire data source sets is possible.

In addition to their advantage for noise robustness, the graph models generated by the modified GCNN technique provides greater interpretability than alternative graph models such as tensor factor models.

The modified graph-based technique, or modified GCNN technique with attention according to the invention improves upon GCNN techniques by adding a parameter or attention weights that allows the network to learn how much to trust an edge during training. Further, this allows new methods of visualizations and investigations, including ranking the influencers of a node, inferring the greatest drivers of a link prediction, and possibly even identifying facts which are most likely to alter the prediction of a node. This opens new avenues of considering knowledge bases as living, dynamic collections of facts. Unlike typical link prediction scenarios, the modified GCNN techniques afford an opportunity to separate the data used in the prediction process from the edge prediction itself, allowing for evidence weighting to be considered independently of the prediction task. The modified GCNN and graph models according to the invention demonstrate noisier, cheaper data can be effectively used for more accurate predictions, as well as providing a means for identifying the least-useful facts in the knowledge base. Further, the GNN model with learned attention weights according to the invention has allowed new methods for visualization and interpretation, including ranking the influencers of a node, inferring the greatest drivers of a link prediction, and uncovering errors present in input data sources. Unlike typical link prediction scenarios, GNN models according to the invention based on GCNNs can afford an opportunity to separate the data used in the encoding process from the edge prediction itself, allowing for evidence weighting to be considered independently of the prediction task. Further modifications may include gradient methods or transductive methods being used to examine which unknown facts could be uncovered that would be the largest drivers of change in link prediction score. Such a system begins to approach semi-supervised learning or active learning scenarios, and could even be coupled with reinforcement learning algorithms with a cost on question-answering to probe users for feedback and improve the system.

Figure 5A:
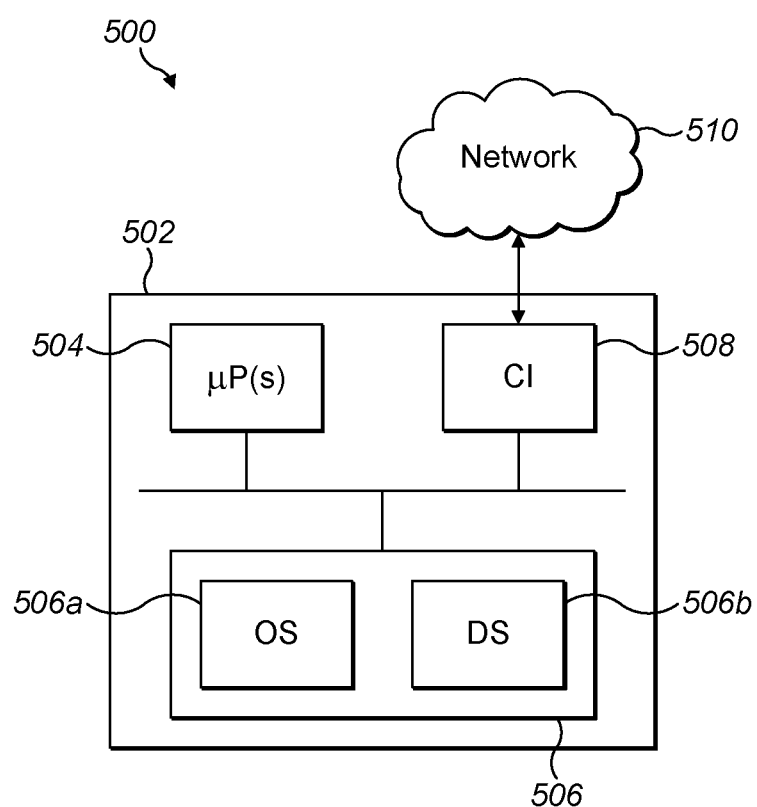
FIG. 5a is a schematic diagram of a computing system according to the invention.

FIG. 5a is a schematic diagram illustrating a computing device 500 that may be used to implement one or more aspects of the modified GCNN technique and/or graph model generation and prediction according to the invention and/or includes the methods, process(es) and/or system(s) and apparatus as described with reference to FIGS. 1a-4b. Computing device 500 includes one or more processor unit(s) 502, memory unit 504 and communication interface 506 in which the one or more processor unit(s) 502 are connected to the memory unit 504 and the communication interface 506. The communications interface 506 may connect the computing device 500 with one or more databases or other processing system(s) or computing device(s). The memory unit 504 may store one or more program instructions, code or components such as, by way of example only but not limited to, an operating system 504a for operating computing device 500 and a data store 504b for storing additional data and/or further program instructions, code and/or components associated with implementing the functionality and/or one or more function(s) or functionality associated with one or more of the method(s) and/or process(es) of the apparatus, module(s), mechanisms and/or system(s)/platforms/architectures as described herein and/or as described with reference to at least one of FIGS. 1a to 4c.

Further aspects of the invention may include one or more apparatus and/or devices that include a communications interface, a memory unit, and a processor unit, the processor unit connected to the communications interface and the memory unit, wherein the processor unit, storage unit, communications interface are configured to perform the system(s), apparatus, method(s) and/or process(es) or combinations thereof as described herein with reference to FIGS. 1a to 4c.

Figure 5B:
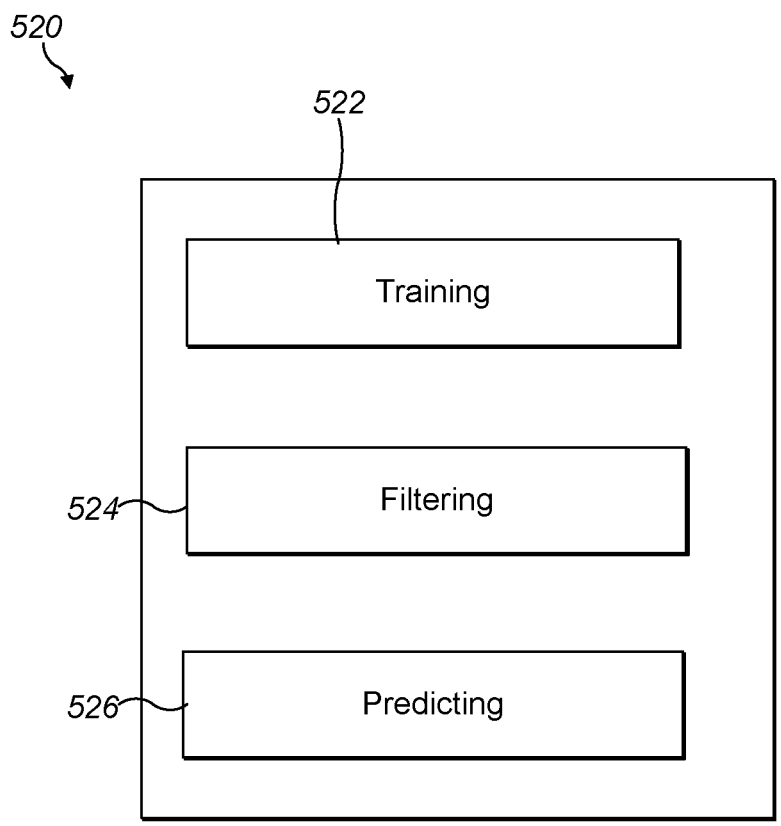
FIG. 5b is a schematic diagram of a system according to the invention.

FIG. 5b is a schematic diagram illustrating a system 520 for generating graph models according to the invention. The system 520 includes an training module 522 configured to train a GNN model based on data representative of at least a portion of an entity-entity graph. The entity-entity graph including a plurality of entity nodes in which each entity node is connected to one or more entity nodes of the plurality of entity nodes by one or more corresponding relationship edges. The weights of the GNN model include an attention weight assigned to each relationship edge of at least the portion of the entity-entity graph, where the attention weights indicate the relevancy of each relationship edge between entity nodes of at least the portion of entity-entity graph. The GNN model may be configured for predicting relationships between two or more entities and one or more relationships. The system 520 further includes an entity-entity graph filtering module 524 configured to receive, from a trained GNN model trained by the training module 522, a set of trained attention weights and generate a filtered entity-entity graph by weighting each edge of at least a portion of the entity-entity graph with the corresponding trained attention weight. The filtering module 524 may generate the filtered entity-entity graph by removing edges weighted by the attention weight of the entity-entity graph if those edges are below a certain predetermined threshold. Alternatively or additionally, the filtering module 524 may generate the filtered entity-entity graph by removing edges of the entity-entity graph if the corresponding attention weights are below or equal to an attention relevancy threshold. The system 520 may further include a prediction module 526 configured to: retrieve a trained GNN model; input to the trained GNN model data representative of a first entity, a second entity and a relationship associated with an entity-entity graph; and receive a prediction score or relationship score from the trained GNN model indicating the likelihood of the first and the second entity having the relationship. The system 520 may include the functionality of the method(s), process(es), and/or system(s) associated with the invention as described herein, or as described with reference to FIGS. 1a-5a for providing a modified GCNN technique, graph models generated therefrom, and/or filtering mechanisms for attention filtering entity-entity graphs, and the like.

The training module 522 may further include an embedding module configured to generate an embedding based on data representative of at least a portion of an entity-entity graph for a GNN model, where the embedding includes an attention weight assigned to each relationship edge of at least the portion of the entity-entity graph; and an update module configured to update weights of the GNN model including the attention weights by minimising a loss function associated with at least the embedding; where the training module is further configured to train another GNN model or update a trained GNN model based on an associated filtered entity-entity graph. The system 520 may include the functionality of the method(s), process(es), and/or system(s) associated with the invention as described herein, or as described with reference to FIGS. 1a-5a for providing a modified GCNN technique, graph models generated therefrom, and/or filtering mechanisms for attention filtering entity-entity graphs, and the like.

In the embodiment described above the server may comprise a single server or network of servers. In some examples the functionality of the server may be provided by a network of servers distributed across a geographical area, such as a worldwide distributed network of servers, and a user may be connected to an appropriate one of the network of servers based upon a user location.

The above description discusses embodiments of the invention with reference to a single user for clarity. It will be understood that in practice the system may be shared by a plurality of users, and possibly by a very large number of users simultaneously.

The embodiments described above are fully automatic. In some examples a user or operator of the system may manually instruct some steps of the method to be carried out.

In the described embodiments of the invention the system may be implemented as any form of a computing and/or electronic device. Such a device may comprise one or more processors which may be microprocessors, controllers or any other suitable type of processors for processing computer executable instructions to control the operation of the device in order to gather and record routing information. In some examples, for example where a system on a chip architecture is used, the processors may include one or more fixed function blocks (also referred to as accelerators) which implement a part of the method in hardware (rather than software or firmware). Platform software comprising an operating system or any other suitable platform software may be provided at the computing-based device to enable application software to be executed on the device.

Various functions described herein can be implemented in hardware, software, or any combination thereof. If implemented in software, the functions can be stored on or transmitted over as one or more instructions or code on a computer-readable medium. Computer-readable media may include, for example, computer-readable storage media. Computer-readable storage media may include volatile or non-volatile, removable or non-removable media implemented in any method or technology for storage of information such as computer readable instructions, data structures, program modules or other data. A computer-readable storage media can be any available storage media that may be accessed by a computer. By way of example, and not limitation, such computer-readable storage media may comprise RAM, ROM, EEPROM, flash memory or other memory devices, CD-ROM or other optical disc storage, magnetic disc storage or other magnetic storage devices, or any other medium that can be used to carry or store desired program code in the form of instructions or data structures and that can be accessed by a computer. Disc and disk, as used herein, include compact disc (CD), laser disc, optical disc, digital versatile disc (DVD), floppy disk, and blu-ray disc (BD). Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, DSL, or wireless technologies such as infrared, radio, and microwave are included in the definition of communication medium. Combinations of the above should also be included within the scope of computer-readable media.

Alternatively, or in addition, the functionality described herein can be performed, at least in part, by one or more hardware logic components. For example, and without limitation, hardware logic components that can be used may include Field-programmable Gate Arrays (FPGAs), Program-specific Integrated Circuits (ASICs), Program-specific Standard Products (ASSPs), System-on-a-chip systems (SOCs). Complex Programmable Logic Devices (CPLDs), etc.

Although illustrated as a single system, it is to be understood that the computing device may be a distributed system. Thus, for instance, several devices may be in communication by way of a network connection and may collectively perform tasks described as being performed by the computing device.

Although illustrated as a local device it will be appreciated that the computing device may be located remotely and accessed via a network or other communication link (for example using a communication interface).

The term 'computer' is used herein to refer to any device with processing capability such that it can execute instructions. Those skilled in the art will realise that such processing capabilities are incorporated into many different devices and therefore the term 'computer' includes PCs, servers, mobile telephones, personal digital assistants and many other devices.

Those skilled in the art will realise that storage devices utilised to store program instructions can be distributed across a network. For example, a remote computer may store an example of the process described as software. A local or terminal computer may access the remote computer and download a part or all of the software to run the program. Alternatively, the local computer may download pieces of the software as needed, or execute some software instructions at the local terminal and some at the remote computer (or computer network). Those skilled in the art will also realise that by utilising conventional techniques known to those skilled in the art that all, or a portion of the software instructions may be carried out by a dedicated circuit, such as a DSP, programmable logic array, or the like.

It will be understood that the benefits and advantages described above may relate to one embodiment or may relate to several embodiments. The embodiments are not limited to those that solve any or all of the stated problems or those that have any or all of the stated benefits and advantages. Variants should be considered to be included into the scope of the invention.

Any reference to 'an' item refers to one or more of those items. The term 'comprising' is used herein to mean including the method steps or elements identified, but that such steps or elements do not comprise an exclusive list and a method or apparatus may contain additional steps or elements.

As used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices.

Further, as used herein, the term "exemplary" is intended to mean "serving as an illustration or example of something".

Further, to the extent that the term "includes" is used in either the detailed description or the claims, such term is intended to be inclusive in a manner similar to the term "comprising" as "comprising" is interpreted when employed as a transitional word in a claim.

The figures illustrate exemplary methods. While the methods are shown and described as being a series of acts that are performed in a particular sequence, it is to be understood and appreciated that the methods are not limited by the order of the sequence. For example, some acts can occur in a different order than what is described herein. In addition, an act can occur concurrently with another act. Further, in some instances, not all acts may be required to implement a method described herein.

Moreover, the acts described herein may comprise computer-executable instructions that can be implemented by one or more processors and/or stored on a computer-readable medium or media. The computer-executable instructions can include routines, sub-routines, programs, threads of execution, and/or the like. Still further, results of acts of the methods can be stored in a computer-readable medium, displayed on a display device, and/or the like.

The order of the steps of the methods described herein is exemplary, but the steps may be carried out in any suitable order, or simultaneously where appropriate. Additionally, steps may be added or substituted in, or individual steps may be deleted from any of the methods without departing from the scope of the subject matter described herein. Aspects of any of the examples described above may be combined with aspects of any of the other examples described to form further examples without losing the effect sought.

It will be understood that the above description of a preferred embodiment is given by way of example only and that various modifications may be made by those skilled in the art. What has been described above includes examples of one or more embodiments. It is, of course, not possible to describe every conceivable modification and alteration of the above devices or methods for purposes of describing the aforementioned aspects, but one of ordinary skill in the art can recognize that many further modifications and permutations of various aspects are possible. Accordingly, the described aspects are intended to embrace all such alterations, modifications, and variations that fall within the scope of the appended claims.

The invention claimed is:

1. A computer-implemented method for training a graph neural network (GNN) model based on an entity-entity graph for relationship prediction, the entity-entity graph comprising a plurality of entity nodes in which each entity node is connected to one or more entity nodes of the plurality of entity nodes by one or more corresponding relationship edges, the method comprising:
   generating an embedding based on data representative of at least a portion of the entity-entity graph for the GNN model, wherein the embedding comprises an attention weight assigned to each relationship edge of at least the portion of the entity-entity graph; and
   updating the GNN model including the attention weights by minimising a loss function $\mathcal{L}(\bullet)$ associated with at least the embedding;
   wherein the attention weights indicate the relevancy of each corresponding relationship edge between entity nodes of the entity-entity graph and assist the GNN model in relationship prediction,
   wherein minimising the loss function, $\mathcal{L}(\cap)$, comprises:
   assigning an attention weight, $\alpha_{r,i,j}$, to each relationship edge of the entity-entity graph, wherein $\alpha_{r,i,j}$ is the attention weight associated with the connection between entity node i and entity node j with relation index r of the plurality of relationships associated with the entity-entity graph;
   modifying the loss function by adding an attention loss function, $\mathcal{L}_{att}(\hat{\Lambda})$ associated with the set of attention weights $\hat{\Lambda}=\{\alpha_{r,i,j}\}$ to the loss function; and
   minimising the modified loss function, $\mathcal{L}_{mod}$, with respect to the weights of the GNN model including the attention weights;
   wherein the modified loss function is $\mathcal{L}_{mod}(\bullet)=\mathcal{L}(\bullet)+\mathcal{L}_{att}(\hat{\Lambda})$.

2. The computer-implemented method as claimed in claim 1, further comprising:
   generating one or more relationship scores based on data representative of one or more embedding(s) associated with the portion of entity-entity graph;
   wherein updating the GNN model further includes updating the GNN model including the attention weights by minimising the loss function based on at least the embedding and the relationship scores.

3. The computer-implemented method as claimed in claim 1, further comprising repeating the steps of generating the embedding and/or scoring, and updating the weights until the GNN model is determined to be trained.

4. The computer-implemented method as claimed in claim 1, wherein the embedding is based on data representative of one or more from the group of:
   at least a portion of the entity-entity graph for the GNN model;
   the entity-entity graph for the GNN model;
   one or more rules defining actions in relation to relationship edges; one or more rules defining actions in relation to entity nodes; and
   one or more rules for including or excluding certain relationship edges or entity nodes.

5. The computer-implemented method as claimed in claim 1, wherein the GNN model is based on one or more neural networks from the group of: one or more artificial NNs; one or more feedforward NNs; one or more recursive NNs; Convolutional NNs; graph NNs; graph CNNs; autoencoder NNs; one or more neural networks capable of being trained based on data representative of the entity-entity graph.

6. The computer-implemented method as claimed in claim 1, wherein an entity node in the entity-entity graph represents any entity from the group of: disease; compound/drug; protein; biological entity; pathway; biological process; cell-line; cell-type; symptom; clinical trials; any other biomedical concept; or any other entity with at least an entity-entity relationship to another entity in the entity-entity graph.

7. The computer-implemented method as claimed in claim 1, further comprising outputting the trained attention weights from the GNN model.

8. The computer-implemented method as claimed in claim 1, further comprising generating a filtered entity-entity graph by weighting each edge with a corresponding trained attention weight.

9. The computer-implemented method as claimed in claim 8, further comprising: updating the GNN model based on the filtered entity-entity graph.

10. The computer-implemented method as claimed in claim 8, further comprising:
    predicting link relationships between entities in the filtered entity-entity relationship graph by inputting to the updated graph model representations of two or more entities; and receiving an indication of the likelihood of a link relationship existing between the two or more entities.

11. The computer-implemented method as claimed in claim 1, further comprising:
predicting link relationships between entities by inputting to the GNN model representations of two or more entities; and
receiving an indication of the likelihood of a link relationship existing between the two or more entities.

12. A computer-implemented method for training a graph neural network (GNN) model based on an entity-entity graph for relationship prediction, the entity-entity graph comprising a plurality of entity nodes in which each entity node is connected to one or more entity nodes of the plurality of entity nodes by one or more corresponding relationship edges, the method comprising:
generating an embedding based on data representative of at least a portion of the entity-entity graph for the GNN model, wherein the embedding comprises an attention weight assigned to each relationship edge of at least the portion of the entity-entity graph;
updating the GNN model including the attention weights by minimising a loss function associated with at least the embedding;
wherein the attention weights indicate the relevancy of each corresponding relationship edge between entity nodes of the entity-entity graph and assist the GNN model in relationship prediction;
outputting the trained attention weights from the GNN model; and
regularising each of the updated attention weights $\alpha_{r,i,j}$, to a normalised attention weight $\alpha'_{r,i,j}$ based on:

$$\alpha'_{r,i,j} = \frac{1}{\Sigma_r \Sigma_j |\alpha_{r,i,j}|} |\alpha_{r,i,j}|$$

wherein the attention weight $\alpha_{r,i,j}$ is initially set to 1 and $\alpha'_{r,i,j} = 1 | \mathcal{N}_i$ for all j prior to training the GNN model.

13. A computer-implemented method for training a graph neural network (GNN) model based on an entity-entity graph for relationship prediction, the entity-entity graph comprising a plurality of entity nodes in which each entity node is connected to one or more entity nodes of the plurality of entity nodes by one or more corresponding relationship edges, the method comprising:
generating an embedding based on data representative of at least a portion of the entity-entity graph for the GNN model, wherein the embedding comprises an attention weight assigned to each relationship edge of at least the portion of the entity-entity graph; and
updating the GNN model including the attention weights by minimising a loss function associated with at least the embedding;
wherein the attention weights indicate the relevancy of each corresponding relationship edge between entity nodes of the entity-entity graph and assist the GNN model in relationship prediction,
wherein the embedding $h_i^{(l+1)}$ for entity node i and layer l+1, for $0 \leq l$ is an N-dimensional vector $h_i^{(l+1)}$ defined by:

$$h_i^{(l+1)} = \sigma\left(\sum_{r \in \mathcal{R}} \sum_{j \in N_i^r} \alpha_{r,i,j} W_{j,j}^{(l)} h_j^{(l)} + b_i^{(l)}\right)$$

where r is a relation index of a relationship from the set of all relationships $\mathcal{R}$ associated with the relationship edges of the entity-entity graph, and j is the index of an entity node connecting to entity node i within $N_i^r$, $N_i^r$ the set of all nodes that connect to entity node i for relation index r, $\alpha_{r,i,j}$ is the attention weight associated with the connection between entity node i and entity node j for relation index r, $b_i^{(l)}$ is a node-specific layer-wise bias vector applied to the embedding $h_i^{(l+1)}$, $W_{j,j}^{(l)}$ is the associated relationship adjacency matrix for the lth layer associated with entity node i, and $\sigma(\bullet)$ is an activation function.

14. The computer-implemented method as claimed in claim 1, wherein the entity-entity graph is generated from a dataset of facts in which each fact is represented by an entity connecting to another entity through a relationship.

15. A graph neural network model obtained from a computer-implemented method according to claim 1.

16. A tangible computer-readable medium comprising data or instruction code for training a graph neural network (GNN) model based on an entity-entity graph for predicting relationships, the entity-entity graph comprising a plurality of entity nodes in which each entity node is connected to one or more entity nodes of the plurality of entity nodes by one or more corresponding relationship edges, which, when executed on one or more processor(s), causes at least one of the one or more processor(s) to perform at least one of the steps of:
generating an embedding based on data representative of at least a portion of the entity-entity graph, wherein the embedding comprises an attention weight assigned to each relationship edge of at least the portion of entity-entity graph; and
updating weights of the GNN model including the attention weights by minimising a loss function $\mathcal{L}(\bullet)$ associated with at least the embedding;
wherein the attention weights indicate the relevancy of each relationship edge between entity nodes of at least the portion of entity-entity graph,
wherein minimising the loss function, $\mathcal{L}(\bullet)$, comprises:
assigning an attention weight, $\alpha_{r,i,j}$, to each relationship edge of the entity-entity graph, wherein $\alpha_{r,i,j}$ is the attention weight associated with the connection between entity node i and entity node j with relation index r of the plurality of relationships associated with the entity-entity graph;
modifying the loss function by adding an attention loss function, $\mathcal{L}_{att}(\hat{\Lambda})$ associated with the set of attention weights $\hat{\Lambda}\{\alpha_{r,i,j}\}$ to the loss function; and
minimising the modified loss function, $\mathcal{L}_{mod}$, with respect to the weights of the GNN model including the attention weights;
wherein the modified loss function is $\mathcal{L}_{mod}(\bullet) = \mathcal{L}(\bullet) + \mathcal{L}_{att}(\hat{\Lambda})$.

17. A tangible computer-readable medium comprising data or instruction code for filtering an entity-entity graph, the entity-entity graph comprising a plurality of entity nodes in which each entity node is connected to one or more entity nodes of the plurality of entity nodes by one or more corresponding relationship edges, which, when executed on one or more processor(s), causes at least one of the one or more processor(s) to perform at least one of the steps of:
receiving, from a graph model generated according to the computer implemented method of claim 1 based on the entity-entity relationship graph, a set of trained attention weights; and filtering the entity-entity relationship graph by weighting each edge with the corresponding trained attention weight.

18. A tangible computer-readable medium comprising computer executable instruction which, when executed on a processor, cause the processor to perform one or more steps of the computer-implemented method of claim 1.

\* \* \* \* \*

UNITED STATES PATENT AND TRADEMARK OFFICE
CERTIFICATE OF CORRECTION

PATENT NO. : 12,106,217 B2  
APPLICATION NO. : 17/041625  
DATED : October 1, 2024  
INVENTOR(S) : Creed et al.

Page 1 of 1

It is certified that error appears in the above-identified patent and that said Letters Patent is hereby corrected as shown below:

In the Claims

• In Claim 1, Column 41, Line 59, replace "$\underline{\mathcal{L}}(\cdot)$" with -- $\mathcal{L}(\cdot)$ --

• In Claim 1, Column 41, Line 65, replace "$\underline{\mathcal{L}}(\cap)$" with -- $\mathcal{L}(\cdot)$ --

• In Claim 1, Column 42, Line 6, replace "$\underline{\mathcal{L}}_{att}(\widehat{\Lambda})$" with -- $\mathcal{L}_{att}(\widehat{\Lambda})$ --

• In Claim 1, Column 22, Line 8, replace "$\underline{\mathcal{L}}_{mod}$," with -- $\mathcal{L}_{mod}$, --

• In Claim 1, Column 42, Line 11-12, replace "$\underline{\mathcal{L}}_{mod}(\cdot) = \underline{\mathcal{L}}(\cdot) + \underline{\mathcal{L}}_{att}(\widehat{\Lambda})$" with -- $\mathcal{L}_{mod}(\cdot) = \mathcal{L}(\cdot) + \mathcal{L}_{att}(\widehat{\Lambda})$ --

• In Claim 13, Column 43, Lines 59-60, replace "layer 1+1" with -- layer $l$ +1 --

• In Claim 13, Column 44, Line 9, replace "$W_{j,j}^{(l)}$" with -- $W_{j,r}^{(l)}$ --

• In Claim 16, Column 44, Line 36, replace "$\underline{\mathcal{L}}(\cdot)$" with -- $\mathcal{L}(\cdot)$ --

• In Claim 16, Column 44, Line 41, replace "$\underline{\mathcal{L}}(\cdot)$" with -- $\mathcal{L}(\cdot)$ --

• In Claim 16, Column 44, Line 49, replace "$\underline{\mathcal{L}}_{att}(\widehat{\Lambda})$" with -- $\mathcal{L}_{att}(\widehat{\Lambda})$ --

• In Claim 16, Column 44, Line 51, replace "$\underline{\mathcal{L}}_{mod}$," with -- $\mathcal{L}_{mod}$, --

• In Claim 16, Column 44, Line 54-55, replace "$\underline{\mathcal{L}}_{mod}(\cdot) = \underline{\mathcal{L}}(\cdot) + \underline{\mathcal{L}}_{att}(\widehat{\Lambda})$" with -- $\mathcal{L}_{mod}(\cdot) = \mathcal{L}(\cdot) + \mathcal{L}_{att}(\widehat{\Lambda})$ --

Signed and Sealed this  
Tenth Day of December, 2024

Katherine Kelly Vidal  
*Director of the United States Patent and Trademark Office*